(12) United States Patent
Abe et al.

(10) Patent No.: US 11,317,896 B2
(45) Date of Patent: May 3, 2022

(54) ULTRASOUND DIAGNOSIS APPARATUS AND IMAGE PROCESSING APPARATUS

(71) Applicant: Toshiba Medical Systems Corporation, Otawara (JP)

(72) Inventors: Yasuhiko Abe, Tochigi (JP); Tetsuya Kawagishi, Tochigi (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 926 days.

(21) Appl. No.: 15/803,261

(22) Filed: Nov. 3, 2017

(65) Prior Publication Data

US 2018/0055487 A1 Mar. 1, 2018

Related U.S. Application Data

(62) Division of application No. 14/490,957, filed on Sep. 19, 2014, now abandoned.

(30) Foreign Application Priority Data

Sep. 30, 2013 (JP) .............................. JP2013-205089

(51) Int. Cl.
*A61B 8/08* (2006.01)
*A61B 8/00* (2006.01)
(Continued)

(52) U.S. Cl.
CPC .......... *A61B 8/5223* (2013.01); *A61B 8/0883* (2013.01); *A61B 8/483* (2013.01);
(Continued)

(58) Field of Classification Search
CPC .................. G06T 7/0012; G06T 7/20; G06T 2207/30048; G06T 7/215; G06T 7/251;
(Continued)

(56) References Cited

U.S. PATENT DOCUMENTS 7,717,852 B2 * 5/2010 Bonnefous ............. A61B 8/488
600/450
2003/0083578 A1 * 5/2003 Abe .................... G01S 15/8993
600/447
(Continued)

FOREIGN PATENT DOCUMENTS

JP 2002-177273 A 6/2002
JP 2003-79627 A 3/2003
(Continued)

OTHER PUBLICATIONS

Office Action dated Mar. 5, 2018 in co-pending U.S. Appl. No. 14/490,957.

(Continued)

*Primary Examiner* — Amelie R Davis
*Assistant Examiner* — Helene Bor
(74) *Attorney, Agent, or Firm* — Oblon, McClelland, Maier & Neustadt, L.L.P.

(57) ABSTRACT

An ultrasound diagnosis apparatus includes a calculating unit, an obtaining unit, a determining unit, and a controlling unit. By using a plurality of pieces of three-dimensional ultrasound image data in a time series corresponding to a three-dimensional region including a myocardium of a subject, the calculating unit calculates first movement information indicating a movement of the myocardium by tracking a movement of a region of interest that corresponds to the myocardium and that is set in each of the plurality of pieces of three-dimensional image data. The obtaining unit obtains direction information indicating a direction of a myocardial fiber in the myocardium. The determining unit determines second movement information indicating a movement of the myocardium with respect to the direction of the myocardial fiber, on the basis of the first movement information and the (Continued)

direction information. The controlling unit causes a display unit to display the second movement information.

11 Claims, 12 Drawing Sheets

(51) Int. Cl.
*G06T 7/215* (2017.01)
*G06T 7/246* (2017.01)

(52) U.S. Cl.
CPC .............. *A61B 8/543* (2013.01); *G06T 7/215* (2017.01); *G06T 7/251* (2017.01); *A61B 8/469* (2013.01); *A61B 8/5207* (2013.01); *G06T 2207/10136* (2013.01); *G06T 2207/30048* (2013.01)

(58) Field of Classification Search
CPC .......... G06T 2207/10136; A61B 8/483; A61B 8/5223; A61B 8/0883; A61B 8/543; A61B 8/469; A61B 8/5207
See application file for complete search history.

(56) References Cited

U.S. PATENT DOCUMENTS

| | | | |
|---|---|---|---|
| 2003/0158483 A1* | 8/2003 | Jackson | A61B 8/0883 600/449 |
| 2003/0171668 A1 | 9/2003 | Tsujino et al. | |
| 2003/0216646 A1* | 11/2003 | Angelsen | A61B 8/145 600/437 |
| 2005/0085729 A1 | 4/2005 | Abe | |
| 2009/0043200 A1 | 2/2009 | Abe | |
| 2009/0083578 A1 | 3/2009 | Nan et al. | |
| 2009/0219301 A1 | 9/2009 | Gerard et al. | |
| 2010/0056919 A1* | 3/2010 | Abe | A61B 8/08 600/443 |
| 2010/0249592 A1* | 9/2010 | Langeland | G06T 7/246 600/443 |
| 2011/0075902 A1* | 3/2011 | Song | A61B 5/02007 382/128 |
| 2011/0190633 A1* | 8/2011 | Kawagishi | A61B 8/08 600/443 |
| 2012/0078097 A1 | 3/2012 | Wang et al. | |
| 2013/0182935 A1 | 7/2013 | Wang et al. | |
| 2013/0197884 A1* | 8/2013 | Mansi | G06T 19/00 703/2 |

FOREIGN PATENT DOCUMENTS

| | | |
|---|---|---|
| JP | 2005-124636 A | 5/2005 |
| JP | 2010-051731 | 3/2010 |
| JP | 2012-187383 A | 10/2012 |

OTHER PUBLICATIONS

Partho P. Sengupta et al., "Left Ventricular Form and Function Revisited: Applied Translational Science to Cardiovascular Ultrasound Imaging", Journal of the American Society of Echocardiography, 2007, 7 pages.
Xenophon Papademetris et al., "Cardiac Image Analysis: Motion and Deformation", SPIE Handbook on Medical Imaging—vol. III: Medical Image Processing and Analysis, Jun. 2000, 36 pages.
Choukri Mekkaoui et al., "Diffusion MRI fractography of the human heart In Vivo at end-diastole and end-systole", Journal of Cardiovascular Magnetic Resonance, 2012, 2 pages.
Hiroshi Ashikaga et al., "Transmural Dispersion of Myofiber Mechanics, Implications for Electrical Heterogeneity In Vivo", Journal of the American College of Cardiology, vol. 49, No. 8, 2007, 8 pages.
Allen Cheng et al., "Heterogeneity of Left Ventricular Wall Thickening Mechanisms", Circulation, 2008, 9 pages.
I. J. Legrice et al. , "Transverse Shear Along Myocardial Cleavage Planes Provides a Mechanism for Normal Systolic Wall Thickening", Circulation Research ,1995, 17 pages.
Wen-Yih I. Tseng et al. "Myocardial Fiber Shortening in Humans: Initial Results of MR Imaging", Radiology, 2000,12 pages.
Choukri Mekkaoui et al. "Fiber architecture in remodeled myocardium revealed with a quantitative diffusion CMR tractography framework and histological validation", JCMR, 2012, 11 pages.
Japanese Office Action dated Mar. 19, 2019 in Japanese Patent Application No. 2018-118248, 3 pages.
Office Action dated Mar. 15, 2019 in co-pending U.S. Appl. No. 14/490,957, 11 pages.
Riyadi, S., et al., "Segmental Boundary Profile of Myocardial Motion to Localize Cardiac Abnormalities" , Proceedings of the World Congress on Engineering, 2010, pp. 692-697 with cover page.
Office Action dated May 26, 2020 in co-pending U.S. Appl. No. 14/490,957, 12 pages.
Office Action dated Apr. 24, 2018 in corresponding Japanese Patent Application No. 2014-177757, 2 pages.
Office Action dated Dec. 28, 2020 in U.S. Appl. No. 14/490,957, filed Sep. 19, 2014.

\* cited by examiner

FIG.6
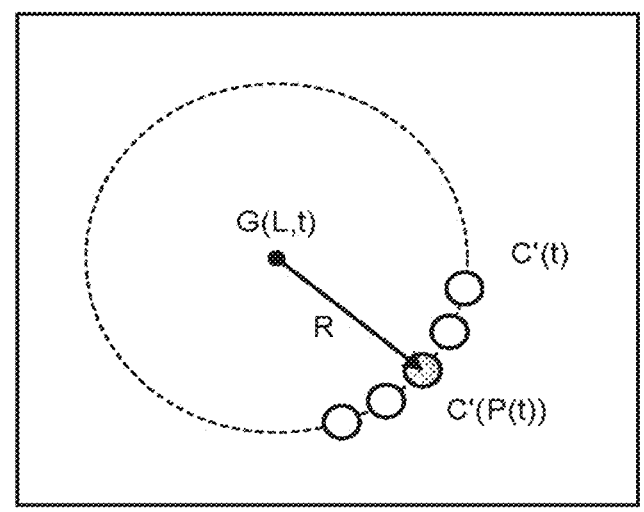
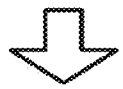
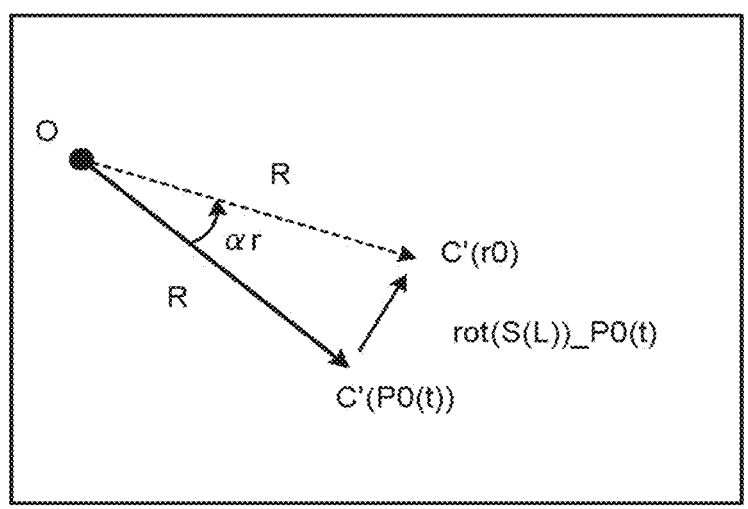

| ENDOCARDIAL PLANE | +60 DEGREES |
|---|---|
| EPICARDIAL PLANE | −60 DEGREES |
| INTERMEDIATE LAYER PLANE | 0 DEGREES |

ULTRASOUND DIAGNOSIS APPARATUS AND IMAGE PROCESSING APPARATUS

CROSS-REFERENCE TO RELATED APPLICATIONS

This application is a divisional of U.S. application Ser. No. 14/490,957, filed on Sep. 19, 2014, based upon and claims the benefit of priority from Japanese Patent Application No. 2013-205089, filed on Sep. 30, 2013, the entire contents of all of which are incorporated herein by reference.

FIELD

Embodiments described herein relate generally to an ultrasound diagnosis apparatus and an image processing apparatus.

BACKGROUND

Even if a fiber strain of individual myocardial cells (myocardial fibers) is as little as approximately "−10% to −15%", the left ventricle, as a whole, can yield an ejection fraction (EF) of 60% or higher. Such mechanics of the heart have been studied since the distant past. The reason for this phenomenon has not yet been definitively explained, but it is believed that the layer structure of the myocardium and the positional arrangement of fiber directions in the myocardium are important factors. Many discussions have been made on this subject in various studies.

As for the layer structure of the myocardium and the fiber directions in the myocardium, it is generally known that, in the middle ("mid") level of the left ventricle, the myocardial fiber direction in the epicardium is a left-hand oblique direction, whereas the myocardial fiber direction in the endocardium is a right-hand oblique direction, and the myocardial fiber direction in the intermediate layer is an annular direction, on the basis of anatomical observations. Further, by implementing methods for analyzing myocardial fiber directions in a non-invasive manner, it is possible to obtain results that are equivalent to the anatomical observations, on the basis of researches that employ Magnetic Resonance Imaging (MRI) apparatuses. Examples of such methods include a method by which myocardial fiber directions are estimated by using a finite element method on the basis of a local myocardial movement obtained by implementing a tagging MRI method. Another example that is used in recent years is a method called "diffusion MRI" by which myocardial fiber directions are estimated by numerically solving a differential equation related to a spatial diffusion in a distribution pattern of water molecules.

Further, in relation to the structure of each of the chambers (e.g., the left ventricle) of the heart, ultrasound diagnosis apparatuses, which is a non-invasive means, have been used to analyze strains in the myocardium in "a radial (wall-thickness) direction, a longitudinal (long-axis) direction, and a circumferential direction" defined by three axes that are orthogonal to each other. More specifically, the analysis of the myocardial strains in the three directions is performed by applying a two- or three-dimensional speckle tracking technique to two- or three-dimensional moving images taken by an ultrasound diagnosis apparatus. The analysis results are used in the clinical field and applied researches.

Strains related to myocardial fiber directions, however, are currently limited to basic research fields such as researches with animal experiments using sonomicrometry and analyses on a short-axis cross-sectional plane using the tagging MRI method.

Further, while analyses using MRI apparatuses are non-invasive and applicable to the clinical field, MRI apparatuses are expensive and large in size. For this reason, it is difficult to make the analyses using MRI apparatuses widespread in the clinical field. Further, the researches using MRI apparatuses described above take labor and computation time to perform the analyses. In addition, MRI apparatuses have restrictions related to time resolution. Thus, MRI apparatuses are not as suitable as ultrasound diagnosis apparatuses for observing dynamics of the heart.

In the current situations, however, no method for checking myocardial fiber directions by using an ultrasound diagnosis apparatus in a non-invasive manner is known. Further, the abovementioned myocardial strains in the various directions using the three axes are designed to define the directions on the basis of the shape of the heart and are not designed to analyze strain components in the myocardial fiber directions.

It has generally been understood that what directly reflects the functions and "viability" of a local myocardium is the "fiber strain", because the strain components in the various directions (in particular, the longitudinal direction and the circumferential direction) can be observed while the "fiber strain (the strain in the myocardial fiber direction)" is being a cause. As explained above, however, ultrasound diagnosis apparatuses are not currently being used for analyzing the "fiber strain" in a non-invasive manner. Further, as for local wall-movement information (e.g., strains), ultrasound diagnosis apparatuses only provide movement components in the specific directions (the radial (wall-thickness) direction, the longitudinal direction, and the circumferential direction) determined by the structure and the shape of the heart.

BRIEF DESCRIPTION OF THE DRAWINGS

FIG. 4, FIG. 5, and FIG. 6 are drawings for explaining the pre-processing process performed by the obtaining unit;

DETAILED DESCRIPTION

An ultrasound diagnosis apparatus according to an embodiment includes a calculating unit, an obtaining unit, a determining unit, and a controlling unit. By using a plurality of pieces of three-dimensional ultrasound image data in a time series corresponding to a three-dimensional region including a myocardium of a subject, the calculating unit calculates first movement information indicating a movement of the myocardium by tracking a movement of a region of interest that corresponds to the myocardium and that is set in each of the plurality of pieces of three-dimensional image data. The obtaining unit obtains direction information indicating a direction of a myocardial fiber in the myocardium. The determining unit determines second movement information indicating a movement of the myocardium with respect to the direction of the myocardial fiber, on the basis of the first movement information and the direction information. The controlling unit causes a display unit to display the second movement information.

Exemplary embodiments of the ultrasound diagnosis apparatus will be explained in detail below, with reference to the accompanying drawings.

First Embodiment

Figure 1:
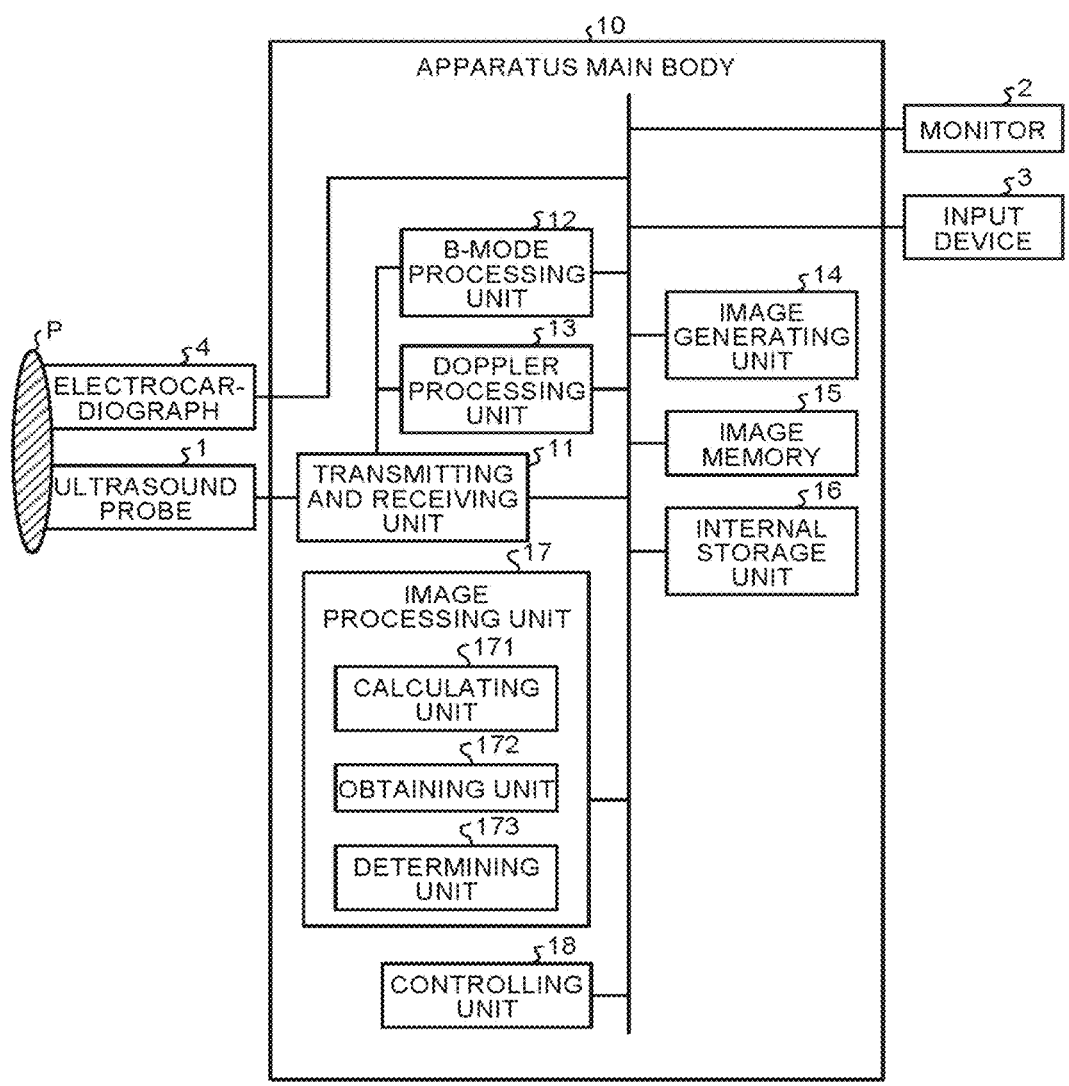
FIG. 1 is a block diagram of an exemplary configuration of an ultrasound diagnosis apparatus according to a first embodiment.

First, a configuration of an ultrasound diagnosis apparatus according to a first embodiment will be explained. FIG. 1 is a block diagram of an exemplary configuration of an ultrasound diagnosis apparatus according to the first embodiment. As illustrated in FIG. 1, the ultrasound diagnosis apparatus according to the first embodiment includes an ultrasound probe 1, a monitor 2, an input device 3, an electrocardiograph 4, and an apparatus main body 10.

The ultrasound probe 1 includes a plurality of transducer elements (e.g., piezoelectric transducer elements), which generate an ultrasound wave on the basis of a drive signal supplied from a transmitting and receiving unit 11 included in the apparatus main body 10 (explained later). Further, the ultrasound probe 1 receives a reflected wave from a subject P and to convert the received reflected wave into an electric signal. Further, the ultrasound probe 1 includes matching layers included in the transducer elements, as well as a backing member that prevents ultrasound waves from propagating rearward from the transducer elements. The ultrasound probe 1 is detachably connected to the apparatus main body 10.

When an ultrasound wave is transmitted from the ultrasound probe 1 to the subject P, the transmitted ultrasound wave is repeatedly reflected on a surface of discontinuity of acoustic impedances at a tissue in the body of the subject P and is received as a reflected-wave signal by the plurality of piezoelectric transducer elements included in the ultrasound probe 1. The amplitude of the received reflected-wave signal is dependent on the difference between the acoustic impedances on the surface of discontinuity on which the ultrasound wave is reflected. When the transmitted ultrasound pulse is reflected on the surface of a flowing bloodstream or a cardiac wall, the reflected-wave signal is, due to the Doppler effect, subject to a frequency shift, depending on a velocity component of the moving members with respect to the ultrasound wave transmission direction.

In the exemplary embodiments described below, the ultrasound probe 1 connected to the apparatus main body 10 is an ultrasound probe that is capable of two-dimensionally scanning the subject P and three-dimensionally scanning the subject P, by using ultrasound waves. More specifically, the ultrasound probe 1 connected to the apparatus main body 10 may be a mechanical four-dimensional (4D) probe or a two-dimensional (2D) array probe. The mechanical 4D probe is able to two-dimensionally scan the subject P by employing the plurality of piezoelectric transducer elements arranged in a row and is also able to three-dimensionally scan the subject P by causing the plurality of piezoelectric transducer elements to swing at a predetermined angle (a swinging angle). The 2D array probe is able to three-dimensionally scan the subject P by employing the plurality of piezoelectric transducer elements arranged in a matrix formation. In addition, the 2D array probe is also able to two-dimensionally scan the subject P by transmitting ultrasound waves in a converged manner.

The input device 3 includes a mouse, a keyboard, a button, a panel switch, a touch command screen, a foot switch, a trackball, a joystick, and the like. The input device 3 receives various types of setting requests from an operator of the ultrasound diagnosis apparatus and to transfer the received various types of setting requests to the apparatus main body 10.

The monitor 2 displays a Graphical User Interface (GUI) used by the operator of the ultrasound diagnosis apparatus to input the various types of setting requests through the input device 3 and to display ultrasound image data and the like generated by the apparatus main body 10.

The electrocardiograph 4 obtains an electrocardiogram (ECG) of the subject P, as a biological signal of the subject P who is three-dimensionally scanned. The electrocardiograph 4 transmits the obtained electrocardiogram to the apparatus main body 10.

The apparatus main body 10 is an apparatus that generates ultrasound image data on the basis of the reflected-wave signal received by the ultrasound probe 1. The apparatus main body 10 illustrated in FIG. 1 is an apparatus that is able to generate two-dimensional ultrasound image data on the basis of two-dimensional reflected-wave data. Further, the apparatus main body 10 illustrated in FIG. 1 is an apparatus that is able to generate three-dimensional ultrasound image data on the basis of three-dimensional reflected-wave data. In the following sections, three-dimensional ultrasound image data may be referred to as "volume data".

As illustrated in FIG. 1, the apparatus main body 10 includes the transmitting and receiving unit 11, a B-mode processing unit 12, a Doppler processing unit 13, an image generating unit 14, an image memory 15, an internal storage unit 16, an image processing unit 17, and a controlling unit 18.

The transmitting and receiving unit 11 includes a pulse generator, a transmission delaying unit, a pulser, and the like and supplies the drive signal to the ultrasound probe 1. The pulse generator repeatedly generates a rate pulse for forming a transmission ultrasound wave at a predetermined rate frequency. Further, the transmission delaying unit applies a delay period that is required to focus the ultrasound wave generated by the ultrasound probe 1 into the form of a beam and to determine transmission directionality and that corresponds to each of the transducer elements, to each of the rate pulses generated by the pulse generator. Further, the pulser applies a drive signal (a drive pulse) to the ultrasound probe 1 with timing based on the rate pulses. In other words, the transmission delaying unit arbitrarily adjusts the transmission directions of the ultrasound waves transmitted from the transducer element surfaces, by varying the delay periods applied to the rate pulses.

The transmitting and receiving unit 11 has a function to be able to instantly change the transmission frequency, the transmission drive voltage, and the like, for the purpose of executing a predetermined scanning sequence on the basis of an instruction from the controlling unit 18 (explained later). In particular, the configuration to change the transmission drive voltage is realized by using a linear-amplifier-type transmitting circuit of which the value can be instantly switched or by using a mechanism configured to electrically switch between a plurality of power source units.

The transmitting and receiving unit 11 includes a pre-amplifier, an Analog/Digital (A/D) converter, a reception delaying unit, an adder, and the like and generates reflected-wave data by performing various types of processes on the reflected-wave signal received by the ultrasound probe 1. The pre-amplifier amplifies the reflected-wave signal for each of channels. The A/D converter applies an A/D conversion to the amplified reflected-wave signal. The reception delaying unit applies a delay period required to determine reception directionality to the result of the A/D conversion. The adder performs an adding process on the reflected-wave signals (digital data) to which the delays have been applied by the reception delaying unit, so as to generate the reflected-wave data. As a result of the adding process performed by the adder, reflected components from the direction corresponding to the reception directionality of the reflected-wave signals are emphasized. A comprehensive beam used in an ultrasound transmission/reception is thus formed according to the reception directionality and the transmission directionality.

When a two-dimensional scan is performed on the subject P, the transmitting and receiving unit 11 causes the ultrasound probe 1 to transmit two-dimensional ultrasound beams. The transmitting and receiving unit 11 then generates two-dimensional reflected-wave data from the two-dimensional reflected-wave signals received by the ultrasound probe 1. When a three-dimensional scan is performed on the subject P, the transmitting and receiving unit 11 causes the ultrasound probe 1 to transmit three-dimensional ultrasound beams. The transmitting and receiving unit 11 then generates three-dimensional reflected-wave data from the three-dimensional reflected-wave signals received by the ultrasound probe 1.

Output signals from the transmitting and receiving unit 11 can be in a form selected from various forms. For example, the output signals may be in the form of signals called Radio Frequency (RF) signals that contain phase information or may be in the form of amplitude information obtained after an envelope detection process.

The B-mode processing unit 12 receives the reflected-wave data from the transmitting and receiving unit 11 and generates data (B-mode data) in which the strength of each signal is expressed by a degree of brightness, by performing a logarithmic amplification, an envelope detection process, and the like on the received reflected-wave data.

The Doppler processing unit 13 obtains velocity information from the reflected-wave data received from the transmitting and receiving unit 11 by performing a frequency analysis, extracts bloodstream, tissues, and contrast-agent echo components under the influence of the Doppler effect, and further generates data (Doppler data) obtained by extracting moving member information such as a velocity, a dispersion, a power, and the like, for a plurality of points.

The B-mode processing unit 12 and the Doppler processing unit 13 according to the first embodiment are able to process both two-dimensional reflected-wave data and three-dimensional reflected-wave data. In other words, the B-mode processing unit 12 is able to generate two-dimensional B-mode data from two-dimensional reflected-wave data and to generate three-dimensional B-mode data from three-dimensional reflected-wave data. The Doppler processing unit 13 is able to generate two-dimensional Doppler data from two-dimensional reflected-wave data and to generate three-dimensional Doppler data from three-dimensional reflected-wave data.

The image generating unit 14 generates ultrasound image data from the data generated by the B-mode processing unit 12 and the Doppler processing unit 13. In other words, from the two-dimensional B-mode data generated by the B-mode processing unit 12, the image generating unit 14 generates two-dimensional B-mode image data in which the strength of the reflected wave is expressed by a degree of brightness. Further, from the two-dimensional Doppler data generated by the Doppler processing unit 13, the image generating unit 14 generates two-dimensional Doppler image data expressing the moving member information. The two-dimensional Doppler image data is a velocity image, a dispersion image, a power image, or an image combining these images. Further, the image generating unit 14 is also capable of generating a Doppler waveform in which velocity information of bloodstream and tissues is plotted in a time series, from the Doppler data generated by the Doppler processing unit 13.

In this situation, generally speaking, the image generating unit 14 converts (by performing a scan convert process) a scanning line signal sequence from an ultrasound scan into a scanning line signal sequence in a video format used by, for example, television and generates display-purpose ultrasound image data. More specifically, the image generating unit 14 generates the display-purpose ultrasound image data by performing a coordinate transformation process compliant with the ultrasound scanning mode used by the ultrasound probe 1. Further, as various types of image processing processes other than the scan convert process, the image generating unit 14 performs, for example, an image processing process (a smoothing process) to re-generate a brightness-average image or an image processing process (an edge enhancement process) using a differential filter within images, while using a plurality of image frames obtained after the scan convert process is performed. Further, the image generating unit 14 synthesizes text information of various parameters, scale graduations, body marks, and the like with the ultrasound image data.

In other words, the B-mode data and the Doppler data are the ultrasound image data before the scan convert process is performed. The data generated by the image generating unit 14 is the display-purpose ultrasound image data obtained after the scan convert process is performed. The B-mode data and the Doppler data may also be referred to as raw data.

Further, the image generating unit 14 generates three-dimensional B-mode image data by performing a coordinate transformation process on the three-dimensional B-mode data generated by the B-mode processing unit 12. Further, the image generating unit 14 generates three-dimensional Doppler image data by performing a coordinate transformation process on the three-dimensional Doppler data generated by the Doppler processing unit 13. In other words, the image generating unit 14 generates "the three-dimensional B-mode image data or the three-dimensional Doppler image data" as "three-dimensional ultrasound image data (volume data)".

Further, the image generating unit 14 performs a rendering process on the volume data, to generate various types of two-dimensional image data used for displaying the volume data on the monitor 2. Examples of the rendering process performed by the image generating unit 14 include a process to generate Multi Planar Reconstruction (MPR) image data from the volume data by implementing an MPR method. Other examples of the rendering process performed by the image generating unit 14 include a process to apply a "curved MPR" to the volume data and a process to apply a "maximum intensity projection" to the volume data.

Another example of the rendering process performed by the image generating unit 14 is a Volume Rendering (VR) process to generate two-dimensional image data reflecting three-dimensional information. Yet another example of the rendering process performed by the image generating unit 14 is a surface rendering process to generate Surface Rendering (SR) image data that three-dimensionally renders the shape of the surface of a target of the rendering process.

The image memory 15 is a memory that stores therein the image data generated by the image generating unit 14. Further, the image memory 15 is also able to store therein the data generated by the B-mode processing unit 12 and the Doppler processing unit 13. After a diagnosis process, for example, the operator is able to invoke the B-mode data or the Doppler data stored in the image memory 15, and the invoked data serves as the display-purpose ultrasound image data via the image generating unit 14.

The image generating unit 14 stores the volume data, i.e., the three-dimensional ultrasound image data, and the time at which an ultrasound scan was performed to generate the volume data into the image memory 15, while keeping the electrocardiogram transmitted from the electrocardiograph 4 in correspondence therewith. The image processing unit 17 and the controlling unit 18 (explained later) are able to obtain cardiac phases at the time of the ultrasound scan performed to generate the volume data, by referring to the data stored in the image memory 15.

The internal storage unit 16 stores therein a control computer program (hereinafter, "control program") to realize ultrasound transmissions and receptions, image processing, and display processing, as well as various types of data such as diagnosis information (e.g., patients' IDs, medical doctors' observations), diagnosis protocols, and various types of body marks. Further, the internal storage unit 16 may be used, as necessary, for storing therein any of the image data stored in the image memory 15. Further, it is possible to transfer the data stored in the internal storage unit 16 to an external apparatus via an interface (not shown). Examples of the external apparatus include a personal computer (PC) used by a medical doctor who performs an image diagnosis process, a storage medium such as a compact disk (CD) or a digital versatile disk (DVD), and a printer.

The image processing unit 17 is provided in the apparatus main body 10 for performing a Computer-Aided Diagnosis (CAD) process. The image processing unit 17 obtains the ultrasound image data stored in the image memory 15 and to perform image processing processes thereon to aid diagnosis processes. Further, the image processing unit 17 stores results of the image processing processes into the image memory 15 and/or the internal storage unit 16. Processes performed by functional units included in the image processing unit 17 will be described in detail later.

The controlling unit 18 controls the entire processes performed by the ultrasound diagnosis apparatus. More specifically, on the basis of the various types of setting requests input by the operator via the input device 3 and various types of control programs and various types of data read from the internal storage unit 16, the controlling unit 18 controls processes performed by the transmitting and receiving unit 11, the B-mode processing unit 12, the Doppler processing unit 13, the image generating unit 14, and the image processing unit 17. Further, the controlling unit 18 exercises control so that the monitor 2 displays the display-purpose ultrasound image data stored in the image memory 15 and the internal storage unit 16. Furthermore, the controlling unit 18 exercises control so that the monitor 2 displays processing results obtained by the image processing unit 17.

An overall configuration of the ultrasound diagnosis apparatus according to the first embodiment has thus been explained. The ultrasound diagnosis apparatus according to the first embodiment configured as described above performs the processes described below by employing the image processing unit 17 and the controlling unit 18, for the purpose of conveniently presenting, in a non-invasive manner, information related to myocardial fiber directions and information about local movement components on the myocardial plane across which myocardial fibers extend.

As illustrated in FIG. 1, the image processing unit 17 includes a calculating unit 171, an obtaining unit 172, and a determining unit 173. The calculating unit 171, by using a plurality of pieces of three-dimensional ultrasound image data in a time series corresponding to a three-dimensional region including a myocardium of the subject P, calculates first movement information indicating a movement of the myocardium by tracking a movement of a region of interest that corresponds to the myocardium and that is set in each of the plurality of pieces of three-dimensional image data. For example, the calculating unit 171 calculates the first movement information that is information about the movement of "the 'region of interest' that is set in the myocardium as a three-dimensional tracking target", by performing a process including a three-dimensional pattern matching process on a group of three-dimensional ultrasound image data in a time series generated by performing an ultrasound scan on the heart. More specifically, the region of interest is at least one boundary plane selected from an endocardial plane of the myocardium, an epicardial plane of the myocardium, and an intermediate layer plane of the myocardium.

Further, the obtaining unit 172 obtains direction information indicating the direction of a myocardial fiber in the myocardium. The direction information serves as information indicating the direction of a myocardial fiber in the region of interest. Further, the determining unit 173 determines second movement information indicating a movement of the myocardium with respect to the direction of the myocardial fiber, on the basis of the first movement information and the direction information of the myocardial fiber. More specifically, the obtaining unit 172 according to the first embodiment estimates the direction information indicating the direction of the myocardial fiber in the myocardium, by using the first movement information. Further, the determining unit 173 according to the first embodiment determines the second movement information by using the direction information estimated by the obtaining unit 172.

Further, the controlling unit 18 causes the monitor 2 to display the second movement information. In this situation, if a plurality of regions of interest are each set as the region of interest, the obtaining unit 172 obtains the direction information indicating the direction of a myocardial fiber, for each of the plurality of regions of interest. In the first embodiment, the obtaining unit 172 estimates the direction information indicating the direction of a myocardial fiber for each of a plurality of regions of interest, by using the first movement information of each of the plurality of regions of interest calculated by the calculating unit 171. Further, the determining unit 173 determines a piece of second movement information for each of the plurality of regions of interest. After that, the controlling unit 18 causes the pieces of second movement information corresponding to the plurality of regions of interest to be displayed.

In the following sections, a specific example of the process described above will be explained in detail. The calculating unit 171 calculates the first movement information by tracking the position of each of the regions of interest set in each of the plurality of pieces of three-dimensional image data, by performing a process including a three-dimensional pattern matching process between pieces of image data. More specifically, the calculating unit 171 performs a three-dimensional speckle tracking (hereinafter, "3DT") process on a group of three-dimensional ultrasound image data (three-dimensional moving image data). An example of a speckle tracking method is a method that makes it possible to accurately estimate a movement by, for example, implementing an optical flow method or performing any of various types of spatiotemporal interpolation processes, together with a pattern matching process. Further, there are some other speckle tracking methods by which a movement is estimated without performing any pattern matching process.

Figure 2:
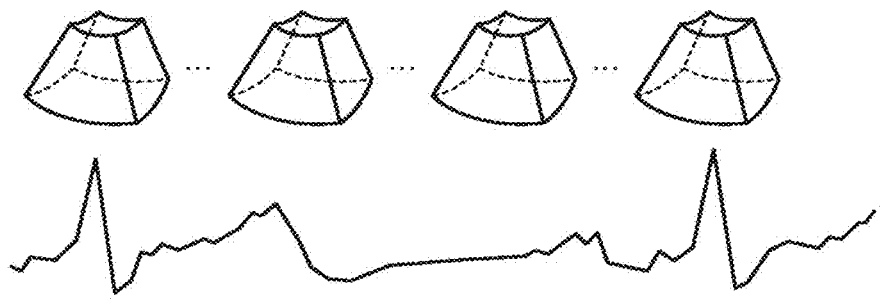
FIG. 2 and FIG. 3 are drawings for explaining the calculating unit.
Figure 3:
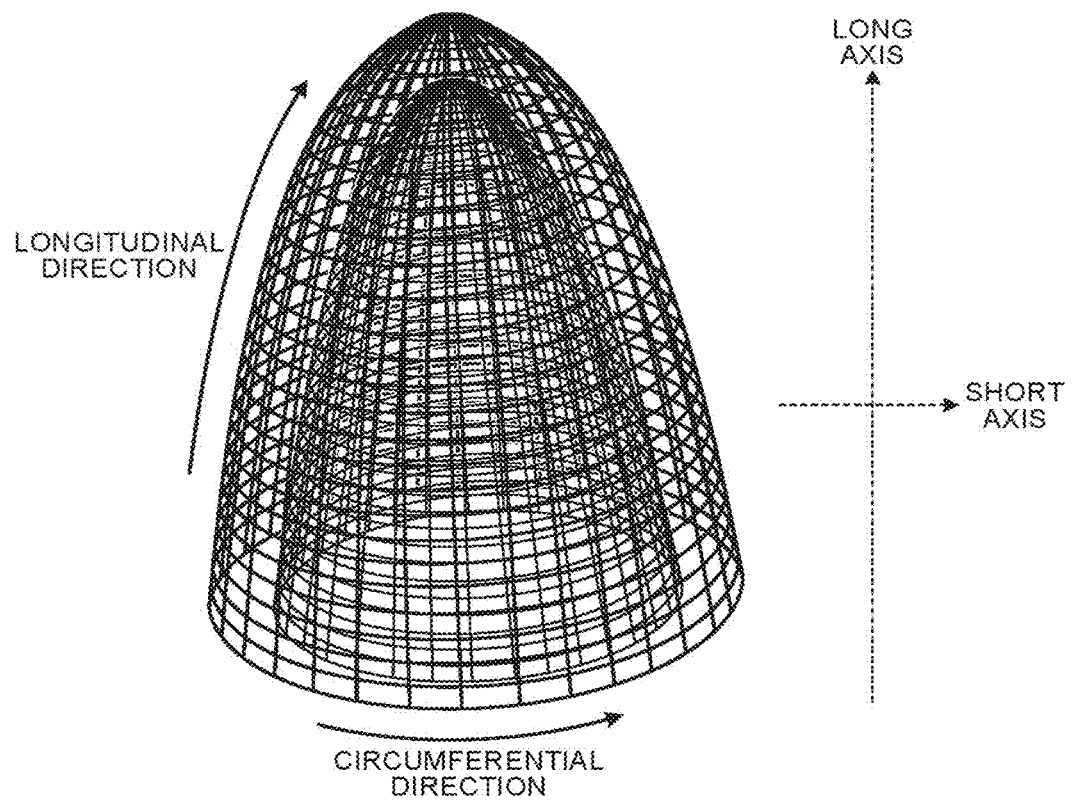

FIGS. 2 and 3 are drawings for explaining the calculating unit. First, by using the ultrasound probe 1 that is capable of performing a three-dimensional scan, the operator three-dimensionally scans, for example, the left-side system of the heart of the subject P for a time period equal to or longer than one heartbeat by an apical approach. As a result, as illustrated in FIG. 2, the image generating unit 14 generates a group of three-dimensional ultrasound image data in a time series corresponding to the time period equal to or longer than one heartbeat and stores the generated group of data into the image memory 15. The group of three-dimensional ultrasound image data described above is a group of three-dimensional B-mode image data.

After that, for example, by using the input device 3, the operator specifies a group of three-dimensional ultrasound image data (time-series data) on which the image processing unit 17 is to perform an analysis and inputs an analysis start request to request the analysis performed by the image processing unit 17. Having received the analysis start request, the controlling unit 18, for example, causes the image generating unit 14 to generate a plurality of pieces of MPR image data obtained by cross-sectioning, on cross-sectional planes extending in multiple directions, the three-dimensional ultrasound image data in the first frame (a first volume) in the group of three-dimensional ultrasound image data and further causes the monitor 2 to display the generated pieces of MPR image data. Further, under control of the controlling unit 18, the calculating unit 171 obtains the group of three-dimensional ultrasound image data serving as the analysis target, from the image memory 15.

Subsequently, by referring to the plurality of pieces of MPR image data displayed on the monitor, the operator sets regions of interest on which a 3DT process is to be performed. For example, the operator traces, within the pieces of MPR image data, the positions of the endocardium of the left ventricle and the epicardium of the myocardium of the left ventricle. After that, for example, the calculating unit 171 reconstructs three-dimensional boundary planes from an endocardial plane and an epicardial plane that were traced. Subsequently, as illustrated in FIG. 3, the calculating unit 171 sets a mesh structured with a plurality of rectangles for each of the endocardial and epicardial planes in the first frame and sets intersection points of the meshes as tracking points. In FIG. 3, the mesh for the epicardial plane is illustrated with line segments that are thicker than the line segments of the mesh for the endocardial plane.

In this situation, for example, the calculating unit 171 may automatically generate the position of the epicardial plane in a position that is apart from the endocardial plane by a predetermined thickness (a predetermined distance). Further, the present embodiment is not limited to the example where the boundary planes that are manually set by the operator are used. Another arrangement is acceptable in which the calculating unit 171 or the controlling unit 18 automatically sets the positions of the boundary planes on the basis of brightness levels or the like of the three-dimensional ultrasound image data.

Further, as illustrated in FIG. 3, for example, the calculating unit 171 sets a coordinate system of the left ventricle including a long axis and a short axis, or the like, on the basis of the shapes of the endocardial plane and the epicardial plane. As a result, as illustrated in FIG. 3, a longitudinal direction of the left ventricle and a circumferential direction of the left ventricle have been set in the three-dimensional ultrasound image data. In addition, as a result of the setting process, a radial (wall-thickness) direction of the left ventricle has also been set. Alternatively, the coordinate system of the left ventricle may manually be set by the operator. Further, in the present embodiment, it is also possible to set a region of interest inside the myocardium by setting an intermediate layer plane between the endocardial plane and the epicardial plane, as a boundary plane serving as a region of interest.

Further, with respect to each of the plurality of tracking points set on the endocardial plane in the first frame, the calculating unit 171 sets template data. Further, with respect to each of the plurality of tracking points set on the epicardial plane in the first frame, the calculating unit 171 sets template data. Each of these pieces of template data is structured with a plurality of voxels centered on the tracking point.

After that, by searching for a region that best matches the speckle pattern in the template data between two frames, the calculating unit 171 tracks the position of the template data by finding out the position into which the template data has moved in the following frame. In other words, the calculating unit 171 tracks the positions of the tracking points by finding out the positions thereof in an n'th frame into which the tracking points in the first frame have moved. As a result, the calculating unit 171 determines the position of a tracking point "P" on the boundary plane at a time "t" for each of all the frames.

In this situation, in the coordinate system illustrated in FIG. 3, the tracking point "P" at the time "t" can be expressed in a position vector space "P=p(C,L)" having a two-dimensional address "the longitudinal direction (L): $1 \leq L \leq M$; the circumferential direction (C): $1 \leq C \leq N$". In the following sections, when a focus is placed on each position address, "C" and "L" will be omitted from the expression, unless noted otherwise.

By performing a 3DT process, the calculating unit 171 calculates a motion vector "V(P(t))" of the tracking point "P(t)" at each of the times "t" by using Expression (1) shown below, as the first movement information. In this situation, "P(t)" denotes a single point in at least one region of interest selected from the endocardial plane, the epicardial plane, and the intermediate layer plane.

$$V(P(t))=P(t+1)-P(t) \qquad (1)$$

After that, the obtaining unit 172 estimates direction information indicating directions of myocardial fibers, by using the local three-dimensional motion vectors (the motion vectors related to the individual tracking points structuring the regions of interest) that were obtained as the first movement information from the 3DT process and that were obtained by performing the process including the three-dimensional pattern matching process performed by the calculating unit 171. The obtaining unit 172 obtains projection components of the motion vectors on the boundary planes serving as the regions of interest and estimates the obtained projection components as the direction information. More specifically, the obtaining unit 172 obtains orthogonal projection components of the motion vectors on the boundary planes and estimates the orthogonal projection components as the direction information. Even more specifically, the obtaining unit 172 estimates the direction information indicating the directions of the myocardial fibers, on the basis of the motion vectors and normal vectors with respect to each of the regions of interest (the boundary planes) near the tracking points at which the motion vectors were obtained. In one example, the obtaining unit 172 obtains the orthogonal projection components of the motion vectors by using the normal vectors on the boundary planes near the tracking points at which the motion vectors were obtained and estimates the orthogonal projection components as the direction information indicating the directions of the myocardial fibers. By the individual orthogonal projection components of the motion vectors at the individual tracking points, a vector field is formed on each of the boundary planes serving as the regions of interest. Further, on the basis of the estimation results, the determining unit 173 determines second movement information that is movement information of the directions of the myocardial fibers.

The process described above is a process based on a hypothesis that "moving directions of the individual tracking points obtained from the 3DT process substantially coincide with the directions of the myocardial fibers" and an objective fact that "the movement components in the radial (wall-thickness) direction are not movement components of the fiber directions". In other words, the process described above is a process of "extracting only the movement components on each of the boundary planes at the origins of the movements, by excluding the movements in the radial (wall-thickness) direction through the orthogonal projection of the individual motion vectors on the boundary plane serving as the region of interest". In the explanation below, the hypothesis presented above will be referred to as "hypothesis (0)".

The process will be explained below, by using mathematical formulae and the like. For example, when a normal vector on the boundary plane including "P(t)" is expressed as "n(P(t))", the obtaining unit 172 calculates an orthogonal projection component "V^(P(t))" of the motion vector "V(P(t))" on the boundary plane including "P(t)" by using Expression (2) shown below:

$$V\char`^(P(t))=V(P(t))-<n(P(t)),V(P(t))>*n(P(t)) \quad (2)$$

In Expression (2), "<n(P(t)),V(P(t))>" denotes the inner product of the normal vector "n(P(t))" and the motion vector "V(P(t))". The orthogonal projection component "V^(P(t))" at each of the tracking points is a motion vector obtained by projecting the motion vector "V(P(t))", which is the first movement information of the tracking point, on the boundary plane serving as the region of interest.

Information obtained from "V^(P(t))" denotes "motion vector information of the myocardium (MyoVector)". Further, in the range where hypothesis (0) explained above is true, it is possible to approximately regard "MyoVector" as the direction of the myocardial fiber "MyoFiber". Accordingly, the simplest exemplary configuration in the first embodiment is to define "MyoVector", without applying any change thereto, as the movement information (the second movement information) indicating the movement of the myocardium with respect to the myocardial fiber, on an assumption that "MyoVector" expresses the direction of the myocardial fiber. This definition will be explained later, as a "first direction definition".

"MyoVector" expresses the movement component on the myocardial plane across which the myocardial fiber extends. It should be noted, however, that the direction of "MyoVector" may not necessarily be equal to "MyoFiber" expressing the direction of the myocardial fiber. For example, a "myocardial sheet sliding theory" is known for explaining a mechanism that causes an increase in the wall thickness. According to this theory, the direction in which a myocardial sheet slides is perpendicular to a myocardial fiber direction. Accordingly, the movement information of the local myocardium includes not only the movement component from the fiber strain (the expansion and contraction) in the fiber direction, but also the movement component from the sheet sliding. The movement component in the direction perpendicular to the myocardial fiber direction is a constraint condition for the exemplary configuration described above. In the following explanation, the constraint condition will be referred to as "constraint condition (A)".

Figure 4:
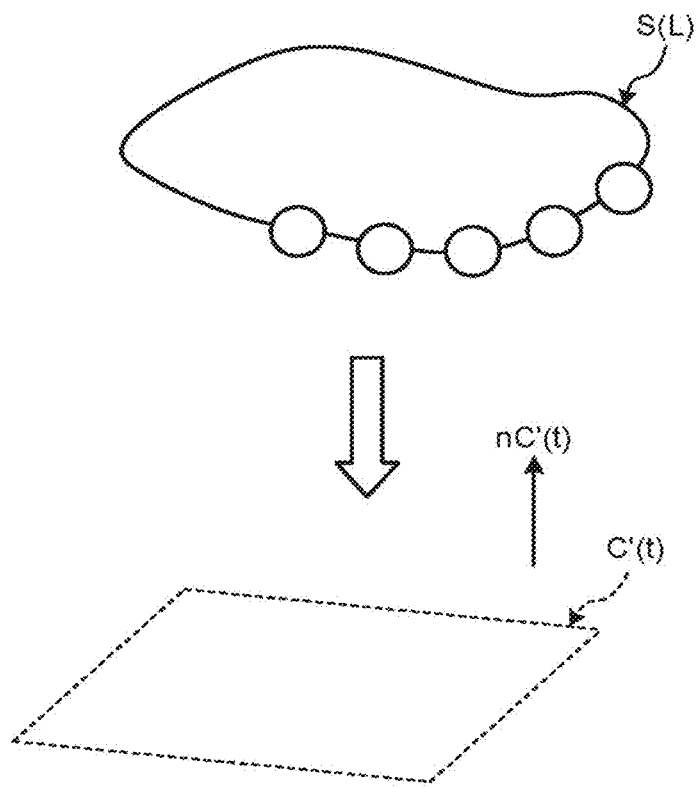
Figure 5:
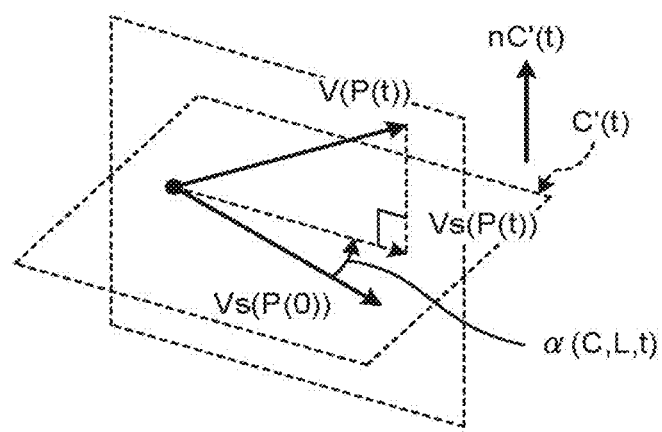

Besides with "constraint condition (A)", there are other various situations where "hypothesis (0)" is not true. To cope with these various situations, the image processing unit 17 according to the first embodiment performs various pre-processing processes explained below. In the following sections, three pre-processing processes (a first pre-processing process, a second pre-processing process, and a third pre-processing process) that are performed to cope with three situations (a first situation, a second situation, and a third situation) where hypothesis (0) is not true, respectively, will be explained, with reference to mathematical formulae and FIGS. 4 to 6. FIGS. 4 to 6 are drawings for explaining the pre-processing processes performed by the obtaining unit.

First, the first situation and the first pre-processing process will be explained. The first situation is a situation where the first movement information is substantially equal to "zero". In other words, in a temporal phase in which the movement of the heart stops, the scalar quantity of the calculated first movement information "V(P(t))" is substantially equal to "zero", while the scalar quantity of "V^(P(t))" used for obtaining the direction information of the myocardial fiber is also substantially equal to "zero". In that situation, the obtaining unit 172 is unable to estimate the direction information of the myocardial fiber.

To cope with this situation, with respect to a temporal phase in which the magnitude of the direction information indicating the direction of the myocardial fiber obtained by performing the estimating process is smaller than a predetermined threshold value, the obtaining unit 172 estimates, as the first pre-processing process, direction information indicating the direction of the myocardial fiber in the temporal phase by performing a temporal interpolation process. For example, if the absolute value (the scalar quantity) of "V^(P(t))" is smaller than a threshold value "Vth" set in advance, the obtaining unit 172 temporally interpolates the value of "V^(P(t))".

For example, to hold data from the past while implementing a temporal interpolation method, the obtaining unit 172 calculates "V^(P(t))" by using Expression (3) shown below.

$$\left. \begin{array}{l} V\char`^(P(t)) = V\char`^(P(t-1)) \\ (\text{Only if ``}|V\char`^(P(t))| < Vth\text{'' is satisfied}) \end{array} \right\} \quad (3)$$

Expression (3) indicates that, if the absolute value of "V^(P(t))" is smaller than the threshold value "Vth", "V^(P (t))" is regarded to be equal to an orthogonal projection component "V^(P(t−1))" obtained at time "t−1".

The calculation using Expression (3) is merely an example. Another arrangement is acceptable in which, with respect to a temporal phase in which the direction information is smaller than a predetermined threshold value, the obtaining unit 172 calculates the direction information in the temporal phase by performing an interpolation process that uses the data in the temporal phase immediately preceding the temporal phase and the data in the temporal phase immediately following the temporal phase. For example, the obtaining unit 172 may use an average vector of "V^(P(t−1))" and "V^(P(t+1))" as "V^(P(t))".

Next, the second situation and the second pre-processing process will be explained. The second situation is a situation in which a translation movement of the entire heart is taken into consideration. For example, during a data acquisition, if the subject P fails to hold his/her breath sufficiently or if fluid gathers in the thoracic cavity in the surrounding of the heart, the heart may move in a swinging motion while using the apex as the base point. The movement component of such a translation movement does not necessarily coincide with a local myocardial fiber direction. For this reason, for the purpose of reducing the impact of the translation movement of the heart, the obtaining unit 172 performs, as the second pre-processing process, a process to eliminate the translation movement component of the entire heart. More specifically, as the second pre-processing process, the obtaining unit 172 obtains a partial translation movement component of the heart from a partial average motion vector in the region of interest and estimates direction information indicating the direction of a myocardial fiber by using a component obtained by subtracting the obtained translation movement component from a motion vector. Even more specifically, the obtaining unit 172 estimates the direction information indicating the direction of the myocardial fiber by using a component obtained by subtracting the translation movement component locally estimated on a short-axis plane that is set in a different position in terms of the longitudinal (long-axis) direction of the region of interest, from a vector component obtained by separating the components of the motion vector in directions on the short-axis plane.

For example, the obtaining unit 172 estimates a translation movement component "Vw(t)" from the motion vector in the region of interest. After that, for example, by using Expression (4) shown below, the obtaining unit 172 calculates "V'^(P(t))" by subtracting "Vw(t)" from "V^(P(t))", which is the motion vector on the boundary plane at each of the tracking points, and estimates the myocardial fiber direction by using calculated "V'^P(t))".

$$V'^{\wedge}(P(t)) = V^{\wedge}(P(t)) - Vw(t) \tag{4}$$

In this situation, because the translation movement component "Vw(t)" expresses the movement component related to the entire heart, it may be effective, for the estimation thereof, to use an average motion vector obtained by averaging the motion vectors within the region of interest. However, because the main factor of the translation movement is considered to be a sideways swinging motion centered on the apex when the left ventricle is imagined to be a hanging bell, it would be impossible to correctly estimate the sideway swinging component, which is supposed to vary in accordance with the distance from the apex, when the "motion vector obtained by averaging the motion vectors within the entirety of the region of interest" were used as the average motion vector.

Accordingly, with respect to a short-axis plane "S(L)" on each short-axis level (L) in the longitudinal (long-axis) direction, the obtaining unit 172 uses an average vector "ave(L)_V(t)" obtained by averaging motion vectors in the circumferential direction at the level. It should be noted that, however, because the movement in the long-axis direction is a valid contraction component, the obtaining unit 172 needs to perform a subtraction between the abovementioned motion vector components, so as not to impact the motion vector component in the long-axis direction.

For this reason, when calculating "ave(L)_V(t)", the obtaining unit 172 extracts a vector component in the direction of the short-axis plane "S(L)" perpendicular to the long-axis direction, from the motion vector "V(P(t))". More specifically, the obtaining unit 172 calculates an orthogonal projection vector component "Vs(P(t))" projected on a regression plane "C'(t)" of "S(L)" by the motion vector "V^(P(t))", which is the orthogonal projection component. In that situation, the obtaining unit 172 calculates a unit normal vector "nC'(t)" on the regression plane "C'(t)".

For example, as illustrated in FIG. 4, the obtaining unit 172 extracts a plurality of tracking points on the endocardial plane passing through the short-axis plane "S(L)" or a plurality of tracking points positioned within a predetermined distance from the endocardial plane passing through the short-axis plane "S(L)". After that, for example, as illustrated in FIG. 4, the obtaining unit 172 calculates the regression plane "C'(t)" by implementing a least-squares method while using the positions of the extracted plurality of tracking points and further calculates the unit normal vector "nC'(t)" from the regression plane "C'(t)".

After that, the obtaining unit 172 obtains "Vs(P(t))" on the short-axis plane "S(L)" by using Expression (5) shown below. The calculation in Expression (5) is the same as the calculation process in Expression (2) used for deriving the orthogonal projection component.

$$Vs(P(t)) = V^{\wedge}(P(t)) - \langle nC'(t), V(P(t)) \rangle * nC'(t) \tag{5}$$

Expression (5) indicates that "Vs(P(t))" is a vector component of the motion vector "V^(P(t))" in the direction of the short-axis plane "S(L)". By using the definition of the position vector space "P=p(C,L)", "Vs(P(t))" can be expressed as "Vs(p(C,L,t))". The obtaining unit 172 obtains "Vs(p(C,L,t))" for each of the tracking points in the circumferential direction using the range "1≤C≤N" and further obtains "ave(L)_V(t)" by calculating an average of the obtained values of "Vs(p(C,L,t))". After that, the obtaining unit 172 determines "ave(L)_V(t)" to be the translation movement component "Vw(t)". In other words, the obtaining unit 172 obtains the translation movement component "Vw(t)" by performing the calculation in Expression (6) shown below.

$$VW(t) = ave(L)\_V(t) = 1/N * \sum_{C=1}^{N} Vs(p(C, L, t)) \tag{6}$$

After that, the obtaining unit 172 estimates the myocardial fiber direction, by assigning "Vw(t)" obtained from Expression (6) to Expression (4) and obtaining "V'^(P(t))" by eliminating the translation movement component from "V^(P(t))".

The process described above (averaging in the circumferential direction) will be further explained. There are two valid movements on the short-axis plane with respect to the longitudinal (long-axis) direction. One is a movement component of a change in the radial (wall-thickness) direction of the myocardium (a radial change of the myocardium) on the short-axis plane. Hereinafter, this movement component will be referred to as a "rad component". The other is a movement component of a rotation on the short-axis plane. Hereinafter, this movement component will be referred to as a "rot component". These two movement components are both point symmetric with respect to the rotation center axis (the gravity point of the boundary plane such as the endocardium or the epicardium) of the short axis, if there is no local abnormality in the wall movement. For this reason, in "ave(L)_V(t)" obtained by averaging the motion vectors on the short-axis plane, the "rad component" and the "rot components" are offset with each other, and the translation movement component, which needs to be eliminated, is extracted as a dominant component.

Next, the third situation and the third pre-processing process will be explained. The third situation is a situation in which "a rotation movement of the heart that can be regarded as a movement perpendicular to the myocardial fiber direction" is taken into consideration. When the myocardial fiber direction temporally changes, the change is observed as a movement component included in the first movement information. However, a "movement component derived from a change in the myocardial fiber direction" makes it difficult for hypothesis (0) described above to be true. In this situation, the "movement component derived from a change in the myocardial fiber direction" corresponds to a torsion, i.e., the rotation component on each short-axis level "L".

To cope with this situation, the obtaining unit 172 performs, as the third pre-processing process, a process to eliminate the rotation component on the basis of a hypothesis that "the rotation direction is substantially perpendicular to the myocardial fiber direction". Hereinafter, this hypothesis will be referred to as "hypothesis (1)".

As the third pre-processing process based on hypothesis (1), the obtaining unit 172 obtains the rotation component on a short-axis plane that is set in a different position in terms of the longitudinal (long-axis) direction of the region of interest, from the motion vector. After that, as the third pre-processing process, the obtaining unit 172 estimates direction information indicating the direction of the myocardial fiber, by using a component obtained by subtracting the obtained rotation component from the motion vector.

More specifically, the obtaining unit 172 first separates the components of the motion vector "V^(P(t))" obtained from the motion vector "V(P(t))" into a vector component "Vx(P(t))" in the long-axis direction and a vector component "Vs(P(t))" in the direction of the short-axis plane "S(L)" orthogonal to the long-axis direction. After that, the obtaining unit 172 estimates a rotation component "rot(S(L))_P(t)" of a vector "Vs(P(t))" on the short-axis plane. Subsequently, the obtaining unit 172 estimates the myocardial fiber direction by using a motion vector "Vs'^(P(t))" obtained by subtracting the rotation component "rot(S(L))_P(t)" from "Vs(P(t))".

In this situation, the final motion vector that is obtained by the obtaining unit 172 as a result of the third pre-processing process to be used for estimating the myocardial fiber direction, i.e., "V'^(P(t))" obtained by eliminating the rotation component from "V^(P(t))" is calculated by using Expression (7) shown below.

$$V'^{\wedge}(P(t))=Vx(P(t))+Vs'^{\wedge}(P(t)) \tag{7}$$

Expression (7) indicates that the final motion vector "V'^(P(t))" is obtained by combining the vector component of "V^(P(t))" in the longitudinal (long-axis) direction with the vector component obtained by subtracting the rotation component on the short-axis plane from the vector component of "V^(P(t))" in the short-axis plane direction.

The third pre-processing process above will be explained further in detail. First, the obtaining unit 172 obtains "Vx(P(t))" by using Expression (8) shown below, while using a unit direction vector "x(L,P(t))" in the longitudinal (long-axis) direction at the tracking point position "P(t)" at the short-axis level "L".

$$Vx(P(t))=<x(L,P(t))V^{\wedge}(P(t))>*x(L,P(t)) \tag{8}$$

Further, the obtaining unit 172 obtains "Vs'^(P(t))" by using Expression (9) shown below. "Vs(P(t))" in Expression (9) is a vector equivalent to "Vs(P(t))" explained in the second situation above. In other words, as illustrated in FIG. 5, "Vs(P(t))" is a vector obtained by projecting "V(P(t))" on the regression plane "C'(t)" by using the unit normal vector "nC'(t)".

$$Vs'^{\wedge}(P(t))=Vs(P(t))-rot(S(L))\_P(t) \tag{9}$$

In this situation, to obtain the rotation component "rot(S(L))_P(t)" in Expression (9), the obtaining unit 172 calculates, as illustrated in FIG. 5, the angle formed by "V(P(t))" and "V(P(t0))". "V(P(t0))" is a vector obtained by projecting "V(P(t0))" in a reference temporal phase "t0" onto "C'(t)" by using the unit normal vector "nC'(t0)". The calculated angle is, as illustrated in FIG. 5, a local rotation angle "α(C,L,t)" of the tracking position "P(t)" on the short-axis plane "S(L)" at the time "t". In FIG. 5, the rotation center used for defining the rotation angle is, for example, the gravity point of "C'(t)" corresponding to the contour on the regression plane. The regression plane and the rotation angle illustrated in FIGS. 4 and 5 are described in detail in Japanese Patent Application Laid-open No. 2010-51731.

Further, the obtaining unit 172 calculates "α(C,L,t)" for each of the tacking points in the circumferential direction, on "C'(t)" corresponding to the contour on the regression plane. After that, the obtaining unit 172 calculates an average rotation angle "α'(L,t)" by averaging "α(C,L,t)" on "C'(t)" in the circumferential direction. In this situation, the rotation angle "αr" used for obtaining "rot(S(L))_P(t)" by performing the process described below may be either the local rotation angle "α(C,L,t)" or the average rotation angle "α'(L,t)". Further, the rotation angle "αr" used in the third pre-processing process may be the value of a rotation angle obtained by calculating an average only in a small area near the point "C'(P(t))=C'(p(C,L,t))" on "C'(t)". For example, the operator is able to select a rotation angle to be used from among these rotation angles, depending on a trade-off between fineness of the spatial resolution of the rotation component to be estimated and spatial stability.

Subsequently, as illustrated in the top section of FIG. 6, the obtaining unit 172 determines the distance "R" between the rotation center "G(L,t)" used for defining the rotation angle and the point "C'(P(t))" on "C'(t)", to be the radius. After that, the obtaining unit 172 obtains a point "C'(r)" in the position reached by rotating the point "C'(P(t))" by the rotation angle "αr".

Subsequently, by using Expression (10) shown below, the obtaining unit 172 calculates the rotation component "rot(S(L))_P(t)" on "C'(t)".

$$rot(S(L))\_P(t)=rot(S(L))\_P0(t)=C'(r0)-C'(P0(t)) \tag{10}$$

In this situation, "C'(r0)" in Expression (10) denotes, as illustrated in the bottom section of FIG. 6, the point at the position corresponding to "C'(r)" when "G(L,t)" is translated to the zero vector "0". Further, "C'(P0(t))" in Expression (10) denotes, as illustrated in the bottom section of FIG. 6, the point at the position corresponding to "C'(P(t))" when "G(L,t)" is translated to the zero vector "0".

As shown in the bottom section of FIG. 6, the obtaining unit 172 obtains "C'(r0)" from "C'(P0(t))" and "αr" that are already known, so as to obtain the rotation component. After that, by assigning "rot(S(L))_P(t)" calculated from Expression (10) to Expression (9), the obtaining unit 172 obtains "Vs'^(P(t))". Subsequently, the obtaining unit 172 calculates "V'^(P(t))" obtained by eliminating the rotation component from "V^(P(t))", by assigning "Vs'^(P(t))" calculated from Expression (9) to Expression (7), so as to determine "V'^(P(t))" to be fiber direction information of the myocardium.

The pre-processing processes performed in the first embodiment to address the three different situations have thus been explained. The first, the second, and the third pre-processing processes performed on the motion vector "V^(P(t))" are all independent processes. Thus, the obtaining unit 172 is also able to obtain the final motion vector by using any of the three pre-processing processes in an arbitrary combination, as necessary. It should be noted that, however, for example, if the operator has determined that there is no need to perform any pre-processing process, the operator may arrange the processes described below to be performed by using the motion vector "V^(P(t))" on which none of the pre-processing processes has been performed.

"V^(P(t))" described in the explanation below may be the motion vector of the orthogonal projection component on which no pre-processing process has been performed or may be the motion vector of the orthogonal projection component that is eventually obtained as a result of any the pre-processing processes.

Further, by using the motion vectors "V^(P(t))" estimated by the obtaining unit 172 as the direction information of the myocardial fiber, the determining unit 173 defines the myocardial fiber direction and further determines the second movement information by using the defined myocardial fiber direction. More specifically, the determining unit 173 determines the myocardial fiber direction by using either a first direction definition or a second direction definition explained below.

According to the first direction definition, the determining unit 173 defines the individual vector structured by the "direction information indicating the direction of the myocardial fiber" on the boundary plane serving as the region of interest, as the myocardial fiber direction. In other words, according to the first direction definition, the motion vector "V^(P(t))" is regarded as the myocardial fiber direction.

In contrast, according to the second direction definition, the determining unit 173 calculates at least one streamline obtained from at least one starting point set on the boundary plane in the vector field formed by the "information indicating the direction of the myocardial fiber" on the boundary plane serving as the region of interest, by performing a spatial interpolation process on the vector field, and further defines the "at least one streamline" as the myocardial fiber direction. More specifically, according to the second direction definition, the determining unit 173 regards a streamline vector "L(t,N)" explained below as the myocardial fiber direction.

The second direction definition will be further explained. First, the determining unit 173 determines an end (at least one of the apex and the valve annulus) in the longitudinal (long-axis) direction in the vector field "V^(P(t))" formed in the region of interest by the motion vector at the individual tracking point obtained from the process described above, to be a starting point "Q0(t)". Alternatively, the determining unit 173 may determine an arbitrary level near the center of the long axis in the vector field "V^(P(t))" to be the starting point "Q0(t)". The position and the quantity of "Q0(t)" may arbitrarily be set by the operator.

After that, the determining unit 173 calculates the value of "V^(Q0(t))" closest to "Q0(t)", by performing a spatial interpolation process on the vector field "V^(P(t))". Subsequently, the determining unit 173 calculates a vector "Q1(t)" to be connected to "Q0(t)" by using Expression (11) shown below.

$$Q1(t)=Q0(t)+V^{\hat{}}(Q0(t)) \quad (11)$$

By sequentially repeating this process on the vector field in the region of interest, the determining unit 173 keeps connecting a vector "Qi(t)" to a vector "Qi−1(t)". After that, either when the extended distance of the connected vectors has reached a predetermined maximum length (e.g., 8 cm) or when the connected vectors has reached the other end in the longitudinal (long-axis) direction, the determining unit 173 en ds the vector connecting process. In this situation, the condition under which the vector connecting process is ended may arbitrarily be set by the operator.

As a result of the process described above, the determining unit 173 obtains one streamline vector for one starting point. The determining unit 173 repeatedly performs the vector connecting process for each of the starting points which are positioned apart from each other and of which the total quantity is N. In a preferable example, the starting points of which the total quantity is N may be a group of starting points obtained by dividing the valve annulus into N sections in the circumferential direction. In that situation, in a preferable example, the determining unit 173 performs a process of preventing each streamline vector from intersecting other streamline vectors that have already been drawn. More specifically, the determining unit 173 performs a process of ending the connecting process when any streamline vector to be connected is detected to intersect another streamline vector. As a result, the determining unit 173 eventually obtains as many streamline vectors "L(t,N)" as N in the region of interest serving as the processing target.

Further, "a definition of the second movement information indicating the movement of the myocardium with respect to the myocardial fiber direction and a method for displaying the second movement information" are realized in, for example, four output modes explained below. Next, a first output mode, a second output mode, a third output mode, and a fourth output mode will be explained, with reference to FIGS. 7 to 11. FIGS. 7 to 11 are drawings for explaining the output modes implemented in the first embodiment. The output modes explained below are realized by a rendering process performed by the image generating unit 14 under control of the controlling unit 18 to which the output information from the determining unit 173 is input.

First, the first output mode will be explained. In the first output mode, the determining unit 173 determines the myocardial fiber directions defined according to either the first direction definition or the second direction definition to be the second movement information and outputs the second movement information to the controlling unit 18.

According to the first direction definition, in the first output mode, the myocardial fiber directions at the tracking points on at least one boundary plane selected from the endocardial plane, the epicardial plane, and the intermediate layer plane that is set as the region of interest is displayed in such a manner that the three-dimensional positions of the tracking points are visible. As a method for realizing the display, it is desirable to implement a 3D rendering display that uses a rendering process performed on volume data. More specifically, to realize the 3D rendering display, the myocardial fiber directions at the tracking points on the boundary plane are displayed by using SR image data obtained by performing an SR process on the boundary plane of three-dimensional ultrasound image data of the heart. Alternatively, the myocardial fiber directions at the tracking points on the boundary plane may be displayed by implementing a map display method that uses a polar map indicating a plurality of segments and that is recommended by the American Society of Echocardiography and the American Heart Association.

More specifically, according to the first direction definition, the determining unit 173 determines the direction information "MyoVector" estimated by the obtaining unit 172 to be the second movement information. In that situation, the determining unit 173 determines the individual vectors in the vector field (i.e., "V^(P(t))" obtained at the tracking points) to be the second movement information, without applying any change thereto. Further, the controlling unit 18 causes either lines or arrows each indicating the direction and the magnitude of the individual vector to be displayed while being superimposed on either three-dimensional rendering image data of the region of interest (the SR image data of the boundary plane) or a polar map of the heart.

Alternatively, according to the first direction definition, the determining unit 173 may determine the directions of "MyoVector" which is the direction information estimated by the obtaining unit 172, to be the second movement information. In that situation, the determining unit 173 determines the directions of the individual vectors in the vector field (i.e., the directions of "V^(P(t))" obtained at the tracking points), to be the second movement information. After that, the controlling unit 18 causes either line segments or arrows each indicating the direction of the individual vector in the vector field and having a regulated length to be displayed while being superimposed on either three-dimensional rendering image data of the region of interest (the SR image data of the boundary plane) or a polar map of the heart.

In other words, according to the first direction definition, in the first output mode, either the line segments or the arrows are used as the display objects that present "V^(P(t))". In that situation, in the former case, the display objects reflect both the magnitude and the direction of the vectors "V^(P(t))". In contrast, in the latter case, only the directions are displayed by the display objects having a predetermined size. In other words, in the former case, information about the magnitude of the motion vectors "V^(P(t))" in each temporal phase is included in the output information. In contrast, in the latter case, the output specializes in the information about the myocardial fiber directions obtained from the motion vectors "V^(P(t))" in each temporal phase.

In the latter case, a normalization process is performed in order to obtain a unit direction vector "n" in the myocardial fiber direction. In other words, in the latter case, the unit direction vector "n" in the myocardial fiber direction is obtained by dividing "V^(P(t))" by the magnitude of "V^(P(t))". During the normalizing process, in a preferable example, it is desirable that the determining unit 173 sets a lower limit value "a" to the magnitude of the motion vector. This is a process that takes into consideration the fact that it is more prone to be influenced by noise when the magnitude of the unit direction vector becomes completely zero due to stoppage of the movement of the heart or when the absolute value of the motion vector "V^(P(t))" is small.

For example, if the magnitude of the motion vector is smaller than the lower limit value "σ", the determining unit 173 outputs the second movement information as "zero". Alternatively, for example, for a temporal phase in which the magnitude of the motion vector is smaller than the lower limit value "a", the determining unit 173 obtains the motion vector in the temporal phase by performing an interpolation process in the time direction (i.e., performing the same process as the one explained above as the first pre-processing process), and outputs the second movement information by using the motion vector obtained from the interpolation process.

The process that uses the lower limit value "a" is also applicable to the former example where "V^(P(t))" is defined as the second movement information, without applying any change thereto.

Figure 7:
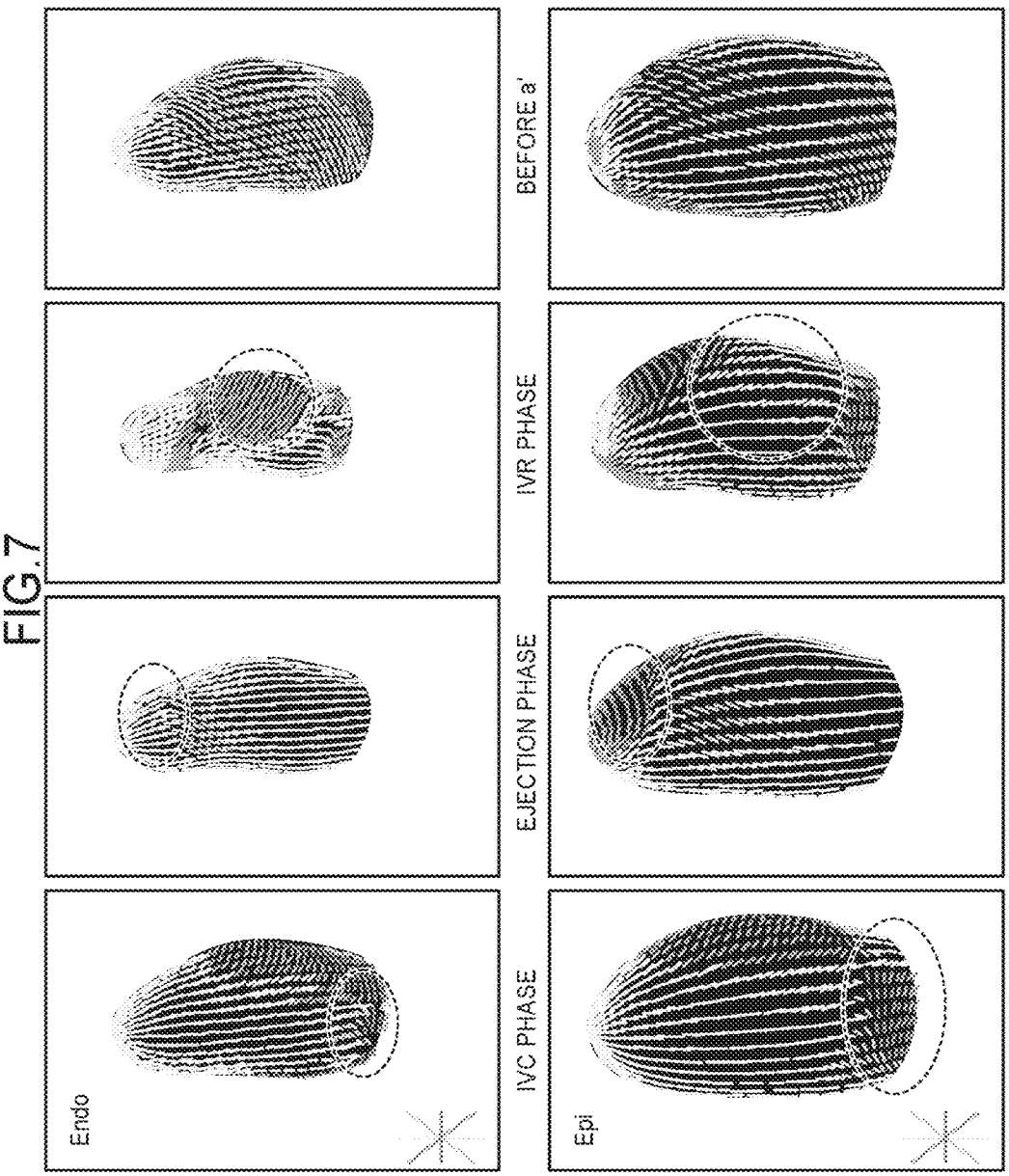
FIG. 7, FIG. 8, FIG. 9, FIG. 10, and FIG. 11 are drawings for explaining the output mode implemented in the first embodiment.

FIG. 7 illustrates an example of the 3D rendering display that uses line segments obtained by normalizing the directions of "V^(P(t))" obtained at the tracking points, while using time-series data of a healthy person as an analysis target. In this situation, the top section of FIG. 7 illustrates images obtained by displaying normalized line segments indicating the myocardial fiber directions at the tracking points on the endocardial plane, so as to be superimposed on SR image data of the endocardium ("Endo") serving as a region of interest. In contrast, the bottom section of FIG. 7 illustrates images obtained by displaying normalized line segments indicating the myocardial fiber directions at the tracking points on the epicardial plane, so as to be superimposed on SR image data of the epicardium ("Epi") serving as another region of interest.

Further, FIG. 7 illustrates the manner in which the directions of the vectors obtained in four representative cardiac phases are distributed. In FIG. 7, "IVC phase" denotes an isovolumetric contraction period; "Ejection phase" denotes a contraction period; "IVR phase" denotes an isovolumetric relaxation period; and "Before a'" denotes a temporal phase immediately before an atrial systole. For the 3D rendering display illustrated in FIG. 7, it is possible to arbitrarily change the position of the line of sight and the direction of the line of sight in accordance with a change request made by the operator. In the present example, the 3D rendering display in FIG. 7 uses the SR image data of the boundary plane in which the boundary position is colored gray (which is shown in black in FIG. 7 for drawing purposes). This process is used for the purpose of avoiding the situation where the visibility of line segments superimposed in the front is lowered by line segments superimposed in the rear.

As illustrated in FIG. 7, because each of the normalized line segments is a line segment indicating the direction of "V^(t))", which is the projection component on the boundary plane, each line segment is displayed in a superimposed manner as if the line segment was adhering on the boundary plane. In this situation, the "areas encircled with dotted lines" in FIG. 7 indicate regions in which the directions of the vectors are significantly different between the endocardium and the epicardium in the different cardiac phases. For example, it is observed from FIG. 7 that the vectors in the apex region during the contraction period are oriented in such a manner that the vectors on the endocardium intersect the vectors on the epicardium.

Displayed at the lower left corner of the upper section and the lower left corner of the lower section of FIG. 7 are "objects each of which formed with four line segments in mutually-different colors". In FIG. 7, differences in the colors among the four line segments are expressed by differences in the darkness. Further, in FIG. 7, each of the line segments shown in the 3D rendering display is displayed while being color-coded, on the basis of the direction of the line segment and the object. The color-coded display is realized according to a display method by which the second output mode is further applied to the first output mode. This display method will be explained in detail with the second output mode.

According to the second direction definition, the determining unit 173 determines "at least one streamline (a streamline vector)" calculated from "MyoVector", which is the direction information estimated by the obtaining unit 172, to be the second movement information. After that, the controlling unit 18 causes lines each corresponding to "at least one streamline (the streamline vector)" to be displayed while being superimposed on either three-dimensional rendering image data of the region of interest or a polar map of the heart. Each of the lines corresponding to the streamline vectors may be a line segment, a curve, or a polygonal line.

Figure 8:
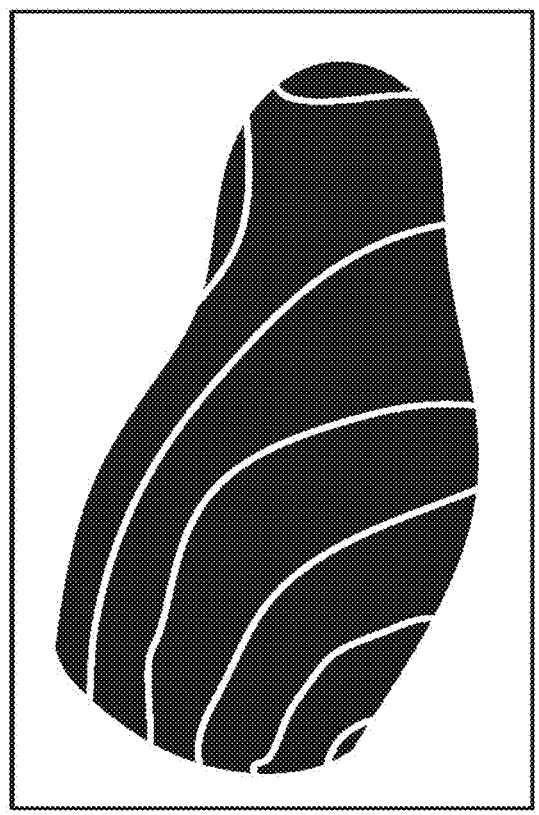
Figure 9:
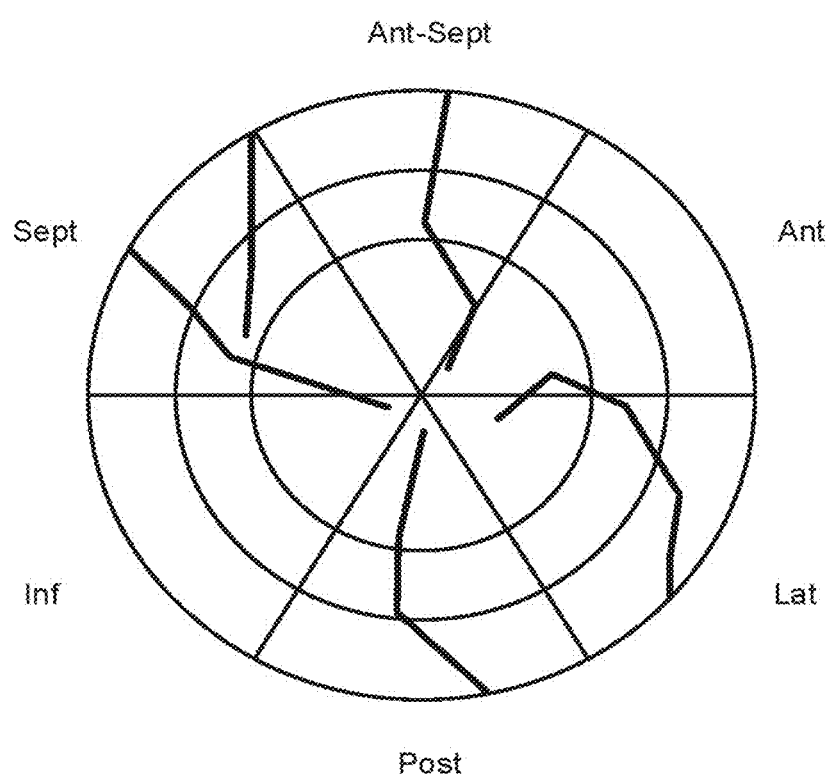

FIG. 8 illustrates an example in which a 3D rendering display using SR image data is applied to a streamline display. FIG. 9 illustrates an example in which a map display using a polar map is applied to a streamline display. In FIG. 9, "Ant-Sept" denotes the anteroseptal wall; "Ant" denotes the anterior wall; "Lat" denotes the lateral wall; "Post" denotes the posterior wall; "Inf" denotes the inferior wall; and "Sept" denotes the septum.

The streamline display illustrated in FIGS. 8 and 9 corresponds to display an image of streamlines along the flow of the fluid, the streamlines formed by ink poured on the plurality of places (the plurality of starting points) in the vector field of the fluid. For the 3D rendering display illustrated in FIG. 8, it is possible to arbitrarily change the position of the line of sight and the direction of the line of sight in accordance with a request made by the operator. Further, the 3D rendering display in FIG. 8 uses SR image data of the boundary plane in which the boundary position is colored gray (which is shown in black in FIG. 8 for drawing purposes). This process is used for the purpose of avoiding the situation where the visibility of streamlines superimposed in the front is lowered by streamlines superimposed in the rear.

Generally speaking, because myocardial fibers are positioned continuously, the streamline vector display illustrated in FIGS. 8 and 9 is more effective in helping the viewer understand the continuous distribution of the fiber vectors than the local display of the individual vectors (see FIG. 7). Further, the map display (the line-segment display and the streamline display using the polar map) has an advantage over the 3D rendering display, because the viewer is able to three-dimensionally understand, all at once, the information about the myocardial fiber directions in the entirety of the region of interest.

The first output mode described above may be realized in a modification example described below in which a plurality of pieces of movement information are displayed simultaneously. In the display output processes explained below, when the plurality of pieces of movement information related to the movement information of the myocardial fiber directions are displayed simultaneously, the operator is able to evaluate the wall movement of the left ventricle in a detailed and comprehensive manner.

As described above, when a plurality of regions of interest are set, the obtaining unit 172 estimates the direction information indicating the direction of the myocardial fiber for each of the plurality of regions of interest. The determining unit 173 determines the second movement information for each of the plurality of regions of interest. After that, when a plurality of regions of interest are set, the controlling unit 18 causes the pieces of second movement information corresponding to the plurality of regions of interest to be displayed while being arranged in rows, as shown in the 3D rendering display illustrated in FIG. 7.

Figure 10:
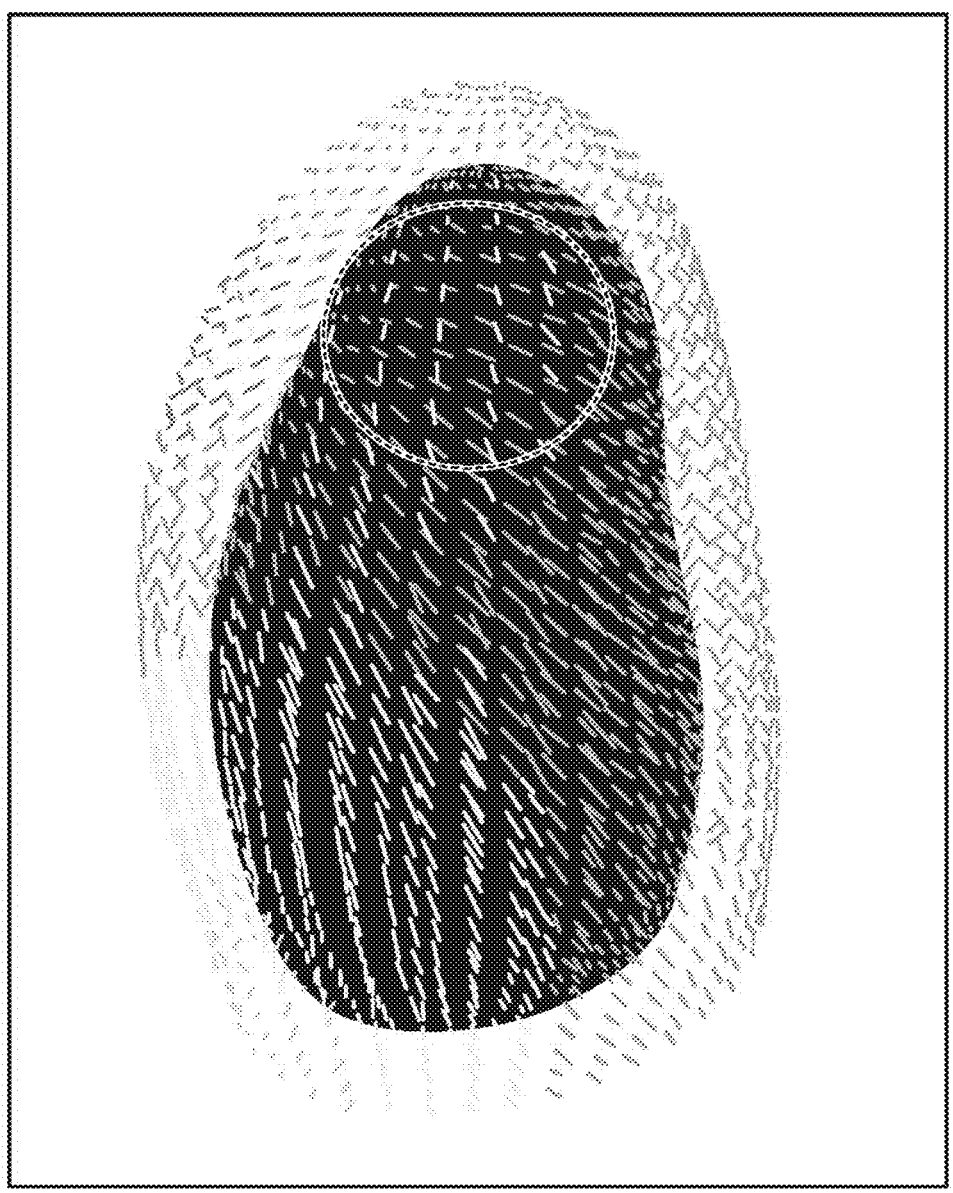

In contrast, in the display modification example of the first output mode, when a plurality of regions of interest are set, the controlling unit 18 may cause the pieces of second movement information corresponding to the plurality of regions of interest to be displayed simultaneously, as shown in a 3D rendering display illustrated in FIG. 10. In FIG. 10, the lines indicating the directions and the magnitudes of the motion vectors "V^(P(t))" obtained at the tracking points of the endocardium are displayed while being superimposed on SR image data of the endocardial plane in which the endocardial plane boundary position is colored gray (which is shown in black in FIG. 10 for drawing purposes). In addition, in FIG. 10, the lines indicating the directions and the magnitudes of the motion vectors "V^(P(t))" obtained at the tracking points of the epicardial plane are also displayed simultaneously while being superimposed on the SR image data of the endocardial plane. The reason why the endocardial plane boundary position is colored gray is the same as explained above. Further, the 3D rendering display illustrated in FIG. 10 is an example of a display to which the second output mode (explained later) is applied.

The rendering simultaneous display illustrated in FIG. 10 makes it possible for the operator to recognize that the fiber vectors (the motion vectors) of the endocardium and the epicardium are substantially in the same directions in the region from the valve annulus to the intermediate level. In addition, by referring to the "region encircled with the dotted line" in FIG. 10, the operator is able to recognize that, in the region near the apex, the directions of the fiber vectors are different between the endocardium and the epicardium, because the directions of the fiber vectors on the endocardial plane are longitudinal direction (the vertical direction), whereas the direction of the fiber vectors on the epicardial plane are circumferential direction (the horizontal direction). Further, the operator is also able to recognize that, in the temporal phase used in the rendering simultaneous display illustrated in FIG. 10, the magnitudes of the motion vectors at the apex are relatively smaller, for both the endocardium and the epicardium. The 3D rendering display illustrated in FIG. 10 is also applicable to a situation where the streamlines on the endocardial plane and the epicardial plane are displayed simultaneously. Further, the 3D rendering display illustrated in FIG. 10 is also applicable to a situation where the directions of "MyoVector" obtained at the tracking points on the endocardial plane and the epicardial plane are displayed simultaneously by using normalized line segments.

Further, in another display modification example of the first output mode, the controlling unit 18 may cause an index related to the local wall movement in the region of interest to be displayed simultaneously together with the second movement information. In an example of a display illustrated in FIG. 11, a 3D rendering display is realized by using line segments obtained by normalizing the myocardial fiber directions, while the endocardial plane boundary position is indicated in gray in the display area on the right-hand side. The 3D rendering display illustrated in FIG. 11 is also an example of a display to which the second output mode (explained later) is applied.

Figure 11:
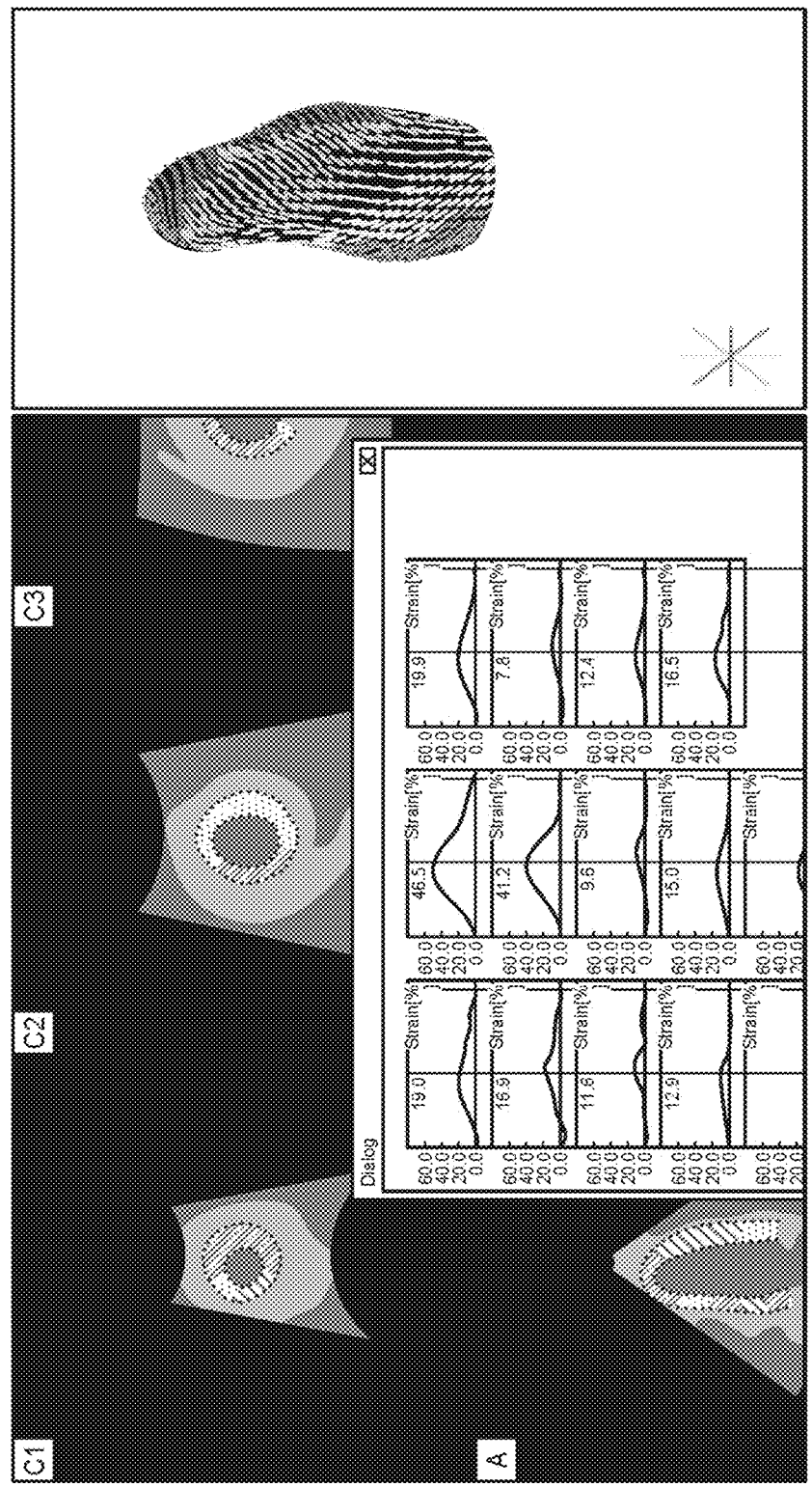

Further, in the example of the display illustrated in FIG. 11, strains are further displayed simultaneously, as conventionally have been displayed, in the display area on the left-hand side, as an index related to the wall movement. In the example illustrated in FIG. 11, information obtained by applying a color conversion to the distribution of "radial strains (RS)" is displayed while being superimposed on a tissue structure represented by a plurality of pieces of MPR image data generated from three-dimensional B-mode image data by using a plurality of cross-sectional planes (plane A, plane B, and plane C at levels 1 to 3). Further, in FIG. 11 time-change curves of the RS are displayed in the charts in units of segments.

The bars extending along the vertical axes in the charts shown in FIG. 11 indicate the temporal phase that is currently being displayed. The operator is able to recognize that the temporal phase in which the information indicated by the various types of image data was obtained is a temporal phase near the end systole at which the RS value reaches a peak. In addition, at the same time, the operator is also able to recognize the appearance of the shapes of the endocardial boundary plane in the temporal phase, as well as the manner in which the directions of the vectors on the endocardium change from the valve annulus toward the apex in a twisted fashion.

Further, besides the examples of the display explained above, in the former modification example explained with reference to FIG. 10, the 3D rendering simultaneous display in which the pieces of information about the endocardium and the epicardium are displayed simultaneously may be realized in such a manner that the line segments (or the arrows) corresponding to the myocardial fiber directions on the endocardial plane and the epicardial plane are displayed in a superimposed manner while the colors thereof are varied. In addition, in the former modification example, the 3D rendering simultaneous display in which the pieces of information about the endocardium and the epicardium are displayed simultaneously may be realized in such a manner that the pieces of information are displayed in a superimposed manner while the degrees of display transparency related to the display objects are varied between the two.

In other words, the controlling unit 18 may cause the pieces of second movement information corresponding to the plurality of regions of interest to be displayed while being superimposed on the three-dimensional rendering image data of a region of interest, by using any display mode in which the regions of interest are distinguishable from each other. As a result of the display control exercised in this manner, for example, the operator is able to more easily identify the myocardial fiber directions on both of the endocardial plane and the epicardial plane.

In the latter modification example explained with reference to FIG. 11, it is acceptable to display, as an index, a distribution of strains on the endocardial plane by applying a color conversion to the RS, a circumferential strain (CS), and a longitudinal strain (LS), for example, and superimposing the strain data on SR image data, while the line segments corresponding to the myocardial fiber directions are displayed simultaneously in a superimposed manner. This modification example is expected to make it easier for the operator to understand a site that is suspected to have a wall movement abnormality on the basis of a low strain value and to understand the appearance of the myocardial fiber directions at such a site. In the description of the first output mode above, the directions in the output information have been referred to as "myocardial fiber directions" for the sake of convenience in the explanation. However, because of the conditions for hypothesis (0) and constraint condition (A) explained at the beginning, the direction information indicated by "MyoVector" obtained in the present embodiment may not necessarily be myocardial fiber directions. In contrast, "MyoVector" is obtained by extracting the information indicating, at least, the movement on the myocardial plane across which the myocardial fibers extend and the directions of the myocardial fibers. For this reason, in the first output mode and other output modes in the embodiments described hereinafter, it is more appropriate to interpret the term "myocardial fiber directions", as "myocardial fiber directions" or "MyoVector directions". When the direction information indicated by "MyoVector" is not direction information indicating the direction of a myocardial fiber, the processes described above performed by "the calculating unit 171, the obtaining unit 172, and the determining unit 173" can be expressed as follows: By using a plurality of pieces of three-dimensional ultrasound image data in a time series corresponding to a three-dimensional region including the myocardium of the subject P, the calculating unit 171 calculates the first movement information (the motion vector) indicating a movement of the myocardium by tracking a movement of the region of interest that is on a predetermined plane of the myocardium and that is set in each of the plurality of pieces of three-dimensional image data. Further, the obtaining unit 172 obtains the vector information (MyoVector) of the projection component of the movement in the region of interest on the predetermined plane of the myocardium, on the basis of the first movement information. After that, the determining unit 173 determines the second movement information indicating the movement of the myocardium, on the basis of the vector information.

Next, the second output mode will be explained. In the second output mode, the determining unit 173 determines a myocardial fiber angle on the basis of the myocardial fiber directions defined according to either the first direction definition or the second direction definition. After that, the determining unit 173 determines the myocardial fiber angle to be second movement information and outputs the second movement information to the controlling unit 18. In other words, the determining unit 173 determines the myocardial fiber angle, which is an angle formed by the myocardial fiber and either the longitudinal direction of the myocardium or the circumferential direction of the myocardium, to be the second movement information. After that, the controlling unit 18 causes the monitor 2 to display the myocardial fiber angle.

More specifically, in the second output mode, the angle (a myocardial fiber angle "θ(t)") formed by the myocardial fiber direction defined according to either the first direction definition or the second direction definition is quantified, at each temporal phase "t", with respect to the longitudinal (long-axis) direction determined at a reference temporal phase "t0", so that "θ(t)" is displayed as the second movement information. Alternatively, in the second output mode, the angle (a myocardial fiber angle "θ(t)") formed by the myocardial fiber direction defined according to either the first direction definition or the second direction definition is quantified, at each temporal phase "t", with respect to the short-axis direction determined at a reference temporal phase "t0", so that "θ(t)" is displayed as the second movement information.

Even more specifically, the determining unit 173 determines a vector in the fiber direction at a target position obtained as either the motion vector "V^(P(t))" according to the first direction definition or the streamline vector "L(t,N)" according to the second direction definition, to be "F(t)".

After that, for example, the determining unit 173 calculates a unit direction vector "c(t0)" in the circumferential direction on the short axis in the same target position in the reference temporal phase. Subsequently, the determining unit 173 calculates the angle "θ(t)" formed by "F(t)" and "c(t0)" and defines the angle "θ(t)" to be the myocardial fiber angle in the target position. In the following sections, "myocardial fiber angle" may simply be referred to as "fiber angle".

In researches using MRI, the directions of fiber angles (the polarities of fiber angles) are defined as follows: a fiber direction parallel to the short axis is the angle "zero"; the counterclockwise direction with respect to the short axis when the left ventricle is viewed from the exterior of the heart is the "positive" direction; the clockwise direction is the "negative" direction; and the direction parallel to the long axis is "±π/2" at maximum. According to this definition, the controlling unit 18 assigns a pink color if the fiber angle with respect to the short-axis direction is "zero degrees", assigns a green color if the fiber angle with respect to the short-axis direction is "±90 degrees", assigns cold colors (blue) if the fiber angle is in the positive direction, and assigns warm colors (red) if the fiber angle is the negative direction.

FIGS. 7, 10, and 11 illustrate the examples of 3D rendering display in which the color assignments are applied to the line segments indicating the myocardial fiber directions. Further, the objects illustrated in FIGS. 7 and 11 serve as objects for informing the operator of the correspondence relationship in the color assignments.

According to the color assignments described above, a fiber angle that is substantially parallel to the long axis is expressed in a color close to green, which expresses "±90 degrees", whereas a fiber angle that is substantially parallel to the short axis is expressed in a color close to pink, which expresses "±0 degrees". As a result, according to the color assignments described above, even if the polarity of the fiber angle changes in a site, it is possible to label the fiber angles in similar colors, and also, it is possible to identify the angles clearly near "±45 degrees" with blue and red.

In the example described above, the range of the fiber angles is defined as "π/2". However, in the display of "MyoVector" in the present embodiment, it is also possible to define the range of the fiber angles by expanding the range to "±π". In that situation, the determining unit 173 obtains a unit direction vector "x(t0)" in the longitudinal (long-axis) direction at the target position in the reference temporal phase and calculates an angle "α(t)" formed by "F(t)" and "x(t0)". After that, the determining unit 173 expands the range by judging the polarity (positive/negative) of "θ(t)" with respect to the long axis, by using "α(t)".

When this definition is used, for example, it is possible to realize a display while the direction of a movement component in the longitudinal direction that moves from the valve annulus toward the direction of the apex during systole is distinguished from the direction of a movement component in the longitudinal direction that, conversely, moves from the apex direction to the valve annulus direction during diastole. In that situation, it is desirable to replace the line segments illustrated in FIG. 7 and the like, with arrows indicating the directions.

As explained above, the second output mode described above is implemented in combination with the first output mode that uses the motion vectors (the projection components) that are the "individual vectors in the vector field" and the streamline vectors represented by "at least one streamline". Accordingly, the processes performed in the second output mode can be summarized as the following three processes:

In a first process in the second output mode, in addition to the motion vectors, the determining unit 173 determines the myocardial fiber angles as the second movement information. After that, the controlling unit 18 changes the display mode of the line segments or the arrows that indicate the directions and the magnitudes of the motion vectors, in accordance with the myocardial fiber angles.

Further, in a second process in the second output mode, in addition to the directions of the motion vectors, the determining unit 173 determines the myocardial fiber angles as the second movement information. After that, the controlling unit 18 changes the display mode of the line segments or the arrows that indicate the directions of the motion vectors, in accordance with the myocardial fiber angles.

Further, in a third process of the second output mode, in addition to the streamline vectors, the determining unit 173 determines the myocardial fiber angles as the second movement information. After that, the controlling unit 18 changes the display mode of the lines corresponding to the streamline vectors, in accordance with the myocardial fiber angles.

The display mode changed in the processes described above is not limited to the one using colors. It is also acceptable to change the thickness of the lines or the arrows, in accordance with the myocardial fiber angles.

Further, besides the examples described above, the second output mode include other examples of display such as an example in which a color conversion is applied to the myocardial fiber angles so as to be displayed in a polar map; and an example in which, while a wall movement index indicating strains or the like is displayed in color, line segments or arrows that are tilted in accordance with the angles formed by the myocardial fiber directions with respect to the long axis (the axis of radiation) direction are simultaneously displayed in a polar map in a superimposed manner.

Next, the third output mode will be explained. In the third output mode, a strain component in the myocardial fiber direction is defined by using the myocardial fiber direction obtained according to either the first direction definition or the second direction definition, and the strain component in the myocardial fiber direction obtained in this manner is determined to be second movement information and output for a display purpose.

In other words, in the third output mode, the determining unit 173 determines the strain in the myocardial fiber direction as the second movement information. More specifically, the determining unit 173 obtains the strain in the myocardial fiber direction by using the direction information and determines the obtained strain as the second movement information. In this situation, in the third output mode, the determining unit 173 calculates the strain component in the myocardial fiber direction by using either a first method or a second method described below.

In the first method, by performing a process that includes a spatial interpolation process, the determining unit 173 obtains an inter-tracking-point distance between each of the tracking points in the region of interest in each temporal phase and one or more tracking points that are positioned in the myocardial fiber direction from the tracking point. After that, the determining unit 173 obtains a strain rate (or an instantaneous rate of change in the distance between the tracking points) on the basis of the obtained distance between the tracking points in each temporal phase. After that, the determining unit 173 time-integrates the obtained strain rates corresponding to the temporal phases, starting from a reference temporal phase over the different temporal phases. Subsequently, by using the value (the time-integrated value) resulting from the time-integration calculation for the temporal phases, the determining unit 173 determines the strain that denotes the rate of change in the length compared to the distance between the tracking points in the reference temporal phase, to be the second movement information.

For example, the determining unit 173 forms a pair made up of: the motion vector "V^(P(t))" obtained at the tracking point "P(t)" in each temporal phase "t"; and a motion vector "V^(Q(t))" obtained at a tracking point "Q(t)" positioned at a predetermined distance from "P(t)" along the myocardial fiber direction. After that, the determining unit 173 calculates a strain rate "SR(P(t))" in the myocardial fiber direction at the tracking point "P(t)" in each temporal phase "t" by using Expression (12) shown below.

$$SR(P(t))=(Vf(P(t))-Vf(Q(t)))/L(t) \qquad (12)$$

In Expression (12), "Vf(t))" denotes a velocity component (unit: m/sec) obtained by dividing "a scalar component obtained from an inner product of the unit direction vector "n" in the myocardial fiber direction and "V^(P(t))" (a scalar component of "V^(P(t))" in the myocardial fiber direction)" by a time period "dT" of the frame intervals serving as the units for the temporal phases. Further, "L(t)" in Expression (12) denotes the distance (unit: m) between the tracking point (P(t)) and the tracking point (Q(t)). Accordingly, the unit for "SR(P(t))" is "1/sec".

Further, the determining unit 173 obtains "Sn(P(t))" indicating the strain in the myocardial fiber direction by time-integrating "SR(P(t))" from the reference temporal phase "t0" to the temporal phase "t". In this situation, "Sn(P(t))" denotes a "natural strain" in the myocardial fiber direction. The "natural strain" may be referred to as a "logarithmic strain" and can be defined as "log(L(t)/L(0))", which is the logarithm of the value obtained by dividing [the distance "L(t)" between the pair of tracking points in each temporal phase] by [the distance "L0" between the pair of tracking points in the reference temporal phase]. The natural strain "Sn(P(t))" is calculated by time-integrating the strain rates in the temporal phases from the reference temporal phase to the corresponding temporal phase.

The determining unit 173 may calculate "$S_L$(P(t))" by converting "Sn(P(t))" by using Expression (13) shown below. "$S_L$(P(t))" denotes a "Lagrangian strain" in the myocardial fiber direction, which indicates a rate of change in the length with respect to the reference temporal phase "t0".

$$S_L(P(t))=\exp(Sn(P(t)))-1 \qquad (13)$$

According to the second method, unlike the calculation process using Expressions (12) and (13), the Lagrangian strain "$S_L$(P(t))" is directly calculated by using the calculation process described below.

More specifically, according to the second method, by performing a process including a spatial interpolation process, the determining unit 173 forms a pair made up of each of the tracking points in the region of interest in the reference temporal phase and a tracking point positioned in the myocardial fiber direction from the tracking point. After that, the determining unit 173 defines a strain calculated as a rate of change in the length comparing the distance between the pair of tracking points in each of the temporal phases other than the reference temporal phase obtained from the tracking results, with the distance between the pair of tracking points in the reference temporal phase, as the second movement information. The "Lagrangian strain" may be referred to as an "engineering strain" and is a value obtained by dividing [the distance "L(t)" between the pair of tracking points in each temporal phase] by [the distance "L0" between the pair of tracking points in the reference temporal phase].

For example, the determining unit 173 forms a pair made up of the tracking point "P(t0)" in the reference temporal phase "t0" and the tracking point "Q(t0)" positioned at a predetermined distance from "P(t0)" along the myocardial fiber direction and further calculates the length "L(t0)" between the tracking point "P(t0)" and the tracking point "Q(t0)". After that, the determining unit 173 calculates the length "L(t)" between the tracking point "P(t)" and the tracking point "Q(t)" in the temporal phase "t" obtained from the tracking results. Subsequently, the determining unit 173 calculates "$S_L$(P(t))" by using Expression (14) shown below.

$$S_L(P(t))=(L(t)-L(t0))/L(t0) \qquad (14)$$

According to the first method and the second method, when forming the pair made up of two points that is necessary for defining the strain in the myocardial fiber direction, there may be some situations where no tracking point is present in the position at the predetermined distance from "P(t)" along the myocardial fiber direction. In those situations, according to the first and the second methods, the determining unit 173 determines the position of "Q(t)" by performing a spatial interpolation process that uses the positions of one or more tracking points that are near the position at the predetermined distance. For example, according to the first and the second methods, the determining unit 173 determines the position of "Q(t)" by performing a spatial interpolation process that uses a group of tracking points "Q'1(t), Q'2(t), . . . , and Q'i(t)" that are near the position at the predetermined distance.

Further, according to the first method, to calculate a motion vector "V^(Q(t))" of "Q(t)" that is not present, a spatial interpolation process is performed by using the motion vectors of one or more tracking points near the position at the predetermined distance. For example, according to the first method, the determining unit 173 calculates "V^(Q(t))" by performing a spatial interpolation process while using a group of motion vectors "V^(Q'1(t)), V^(Q'2(t)), . . . , V^(Q'i(t))" of the abovementioned group of tracking points.

When the spatial interpolation method described above is implemented while "i=4" is satisfied, it is desirable if the determining unit 173 performs a "bi-linear interpolation process".

Further, in the third output mode, the output of the strain component in the fiber direction obtained according to the first method or the second method may be displayed in any of various modes under the display control exercised by the controlling unit 18, in the same manner as a conventional three-axis strain component. Examples of the display modes include a 3D rendering display, a polar map display, and a color display over MPR image data.

In particular, it is desirable to select a display mode in which the strain component in the fiber direction is output at the same time with the information related to the myocardial fiber directions displayed in the first output mode or the second output mode, or at the same time with a conventional wall-movement index (e.g., a three-axis strain component).

The third output mode will be further explained. As explained above, the "fiber strain" indicating the expansion and contraction of individual myocardial fibers has, generally speaking, a value approximately in the range of "−10% to −15%". In contrast, the LS value observed on the endocardium of a healthy person is approximately "−20%", whereas the CS value is approximately "−30%". The LS value and the CS value both have a larger absolute value than the "fiber strain" value. Accordingly, the strain component in the myocardial fiber direction obtained in the third output mode is not necessarily equivalent to the "fiber strain". In other words, the observed strain component in the myocardial fiber direction is larger than the "fiber strain". The reason is, as explained above as "constraint condition (A)", that what is observed as the "fiber strain" is a strain that also takes into account the myocardial deformation component due to the myocardial sheet sliding.

The LS and CS values obtained by implementing conventional methods are strain components in the longitudinal (long-axis) direction and the short-axis direction that are determined on the basis of the shape of the heart. In contrast, the strain component obtained in the third output mode is obtained by extracting the expansion and the contraction components of the myocardium in the myocardial fiber direction. For this reason, the strain component obtained in the third output mode is considered to reflect the functions and "viability" of the local myocardium more directly than the LS and the CS values.

Next, the fourth output mode will be explained. In the fourth output mode, the determining unit 173 estimates either a shear strain rate or a shear strain between a first boundary plane and a second boundary plane, by using vector information of a projection component of a motion vector on the first boundary plane, the motion vector being obtained on the first boundary plane serving as a region of interest, and vector information of a projection component of a motion vector on the second boundary plane, the motion vector being obtained on second boundary plane serving as another region of interest. After that, the determining unit 173 determines either information about the shear strain rate or information about the shear strain, to be second movement information.

More specifically, the determining unit 173 estimates a shear strain rate component between the endocardium and the epicardium, by using "MyoVector" obtained on the endocardial plane serving as a region of interest and "MyoVector" obtained on the epicardial plane serving as another region of interest, further determines information about the obtained shear strain rate component to be the second movement information, and outputs the second movement information for a display purpose. Alternatively, the determining unit 173 determines information about shear strain components obtained by time-integrating the shear strain-rate components between the endocardium and the epicardium to be the second movement information and outputs the second movement information for a display purpose.

For example, in the fourth output mode, the determining unit 173 calculates the shear strain rate component between the endocardium and the epicardium "SRs(P(t))" by using Expression (15) shown below.

$$SRs(P(t)) = (Vf(Pepi(t)) - Vf(Pendo(t)))/W(t) \quad (15)$$

In Expression (15), "Vf(Pepi(t))" denotes a velocity vector (unit: m/sec) obtained by dividing "MyoVector" at a tracking point "Pepi(t)" on the epicardial plane by the time period "dT" of the frame intervals serving as the units for time. Further, in Expression (15), "Vf(Pendo(t))" denotes a velocity vector (unit: m/sec) obtained by dividing "MyoVector" at a tracking point "Pendo(t)" on the endocardial plane by the time period "dT", the tracking point "Pendo(t)" being paired with "Pepi(t)" in a reference temporal phase. Further, in Expression (15), "W(t)" denotes the distance (unit: m) between the tracking point "Pepi(t)" and the tracking point "Pendo(t)", which is the length between the endocardial plane and the epicardial plane. As a result, the unit for "SRs(P(t))" is "1/sec". The output position "P(t)" of "SRs" indicates a tracking point structuring the region of interest within the myocardium, and it is desirable to, for example, assign thereto a corresponding tracking point "Pmid(t)" on the intermediate layer plane.

In this situation, because "MyoVector" is a vector quantity, "SRs" is also a vector quantity. Thus, when the components of "SRs(P(t))" are separated into the circumferential direction and the longitudinal direction that are determined on the basis of the shape of the heart, so as to obtain components such as "SRsC(P(t))" that is a shear strain rate component in the circumferential direction and "SRsL(P(t))" that is a shear strain rate component in the longitudinal direction, the determining unit 173 is able to obtain shear strain rate components as two scalar quantities.

Further, by time-integrating the shear strain rate components such as "SRsC(P(t))" and "SRsL(P(t))", the determining unit 173 is able to obtain a shear strain component according to the definition of the "natural strain" explained above and is also able to convert the component into a shear strain component having the meaning of a "Lagrangian strain". As a result of these processes, the determining unit 173 is able to easily extract, for example, "SsC(P(t))" and "SsL(P(t))" that are shear strain components between the endocardium and the epicardium, by using "MyoVector" obtained in the present embodiment. In the fourth output mode, a focus is placed on the fact that "MyoVector" is the vector information obtained by projecting the motion vector onto the boundary plane serving as a region of interest so that, by using "MyoVector" on the endocardial plane and "MyoVector" on the epicardial plane, it is possible to easily calculate the shear strain rate and the shear strain between the endocardium and the epicardium, which have not conventionally been calculated easily, and to output the calculated information for a display purpose.

The pair made up of regions of interest used as an input in the fourth output mode does not necessarily have to be the endocardium and the epicardium. It is also acceptable to use tracking points "Pmid(t)" on the intermediate layer that are in mutually-different positions within the wall. In that situation, it is possible to analyze shear strain components obtained by dividing the inside of the myocardial wall into detailed sections.

Figure 12:
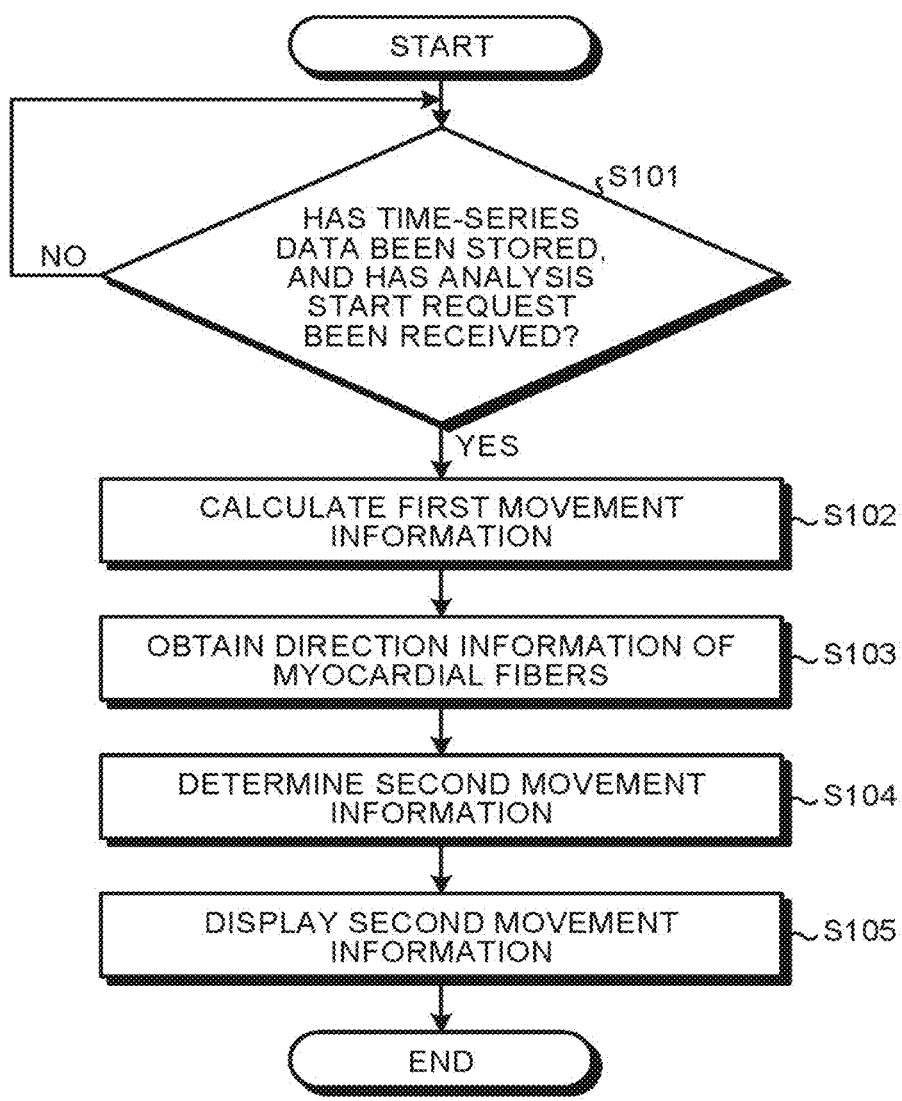
FIG. 12 is a flowchart for explaining an outline of a process performed by the ultrasound diagnosis apparatus according to the first embodiment.

Next, a process performed by the ultrasound diagnosis apparatus according to the first embodiment will be explained, with reference to FIG. 12. FIG. 12 is a flowchart for explaining an outline of the process performed by the ultrasound diagnosis apparatus according to the first embodiment.

As illustrated in FIG. 12, the controlling unit 18 included in the ultrasound diagnosis apparatus according to the first embodiment judges whether time-series data to be an analysis target has been stored and whether an analysis start request has been received (step S101). If no time-series data to be an analysis target has been stored and no analysis start request has been received (step S101: No), the controlling unit 18 stands by until time-series data is stored and an analysis start request is received.

On the contrary, if time-series data to be an analysis target has been stored and an analysis start request has been received (step S101: Yes), the calculating unit 171 calculates the first movement information according to an instruction from the controlling unit 18 (step S102), and the obtaining unit 172 obtains the direction information of myocardial fibers (the direction information indicating directions of the myocardial fibers) (step S103). More specifically, the obtaining unit 172 estimates "V^(P(t))" on the basis of the first movement information. In this situation, the obtaining unit 172 may perform at least one pre-processing process selected from the first, the second, and the third pre-processing processes, on "V^(P(t))".

Further, the determining unit 173 determines second movement information on the basis of a definition that is specified in advance (step S104). In other words, the determining unit 173 defines the myocardial fiber directions on the basis of the direction information according to either the first direction definition or the second direction definition and further determines the second movement information on the basis of the definition specified in one of the output modes selected from the first, the second, the third, and the fourth output modes.

After that, under the control of the controlling unit 18, the monitor 2 displays the second movement information in one of the output modes selected from the first to the fourth output modes (step S105), and the process is ended. At step S105, the second movement information is displayed in a 3D rendering display or a polar map display. These display modes may be realized with a display of a moving picture or a display of still images that are arranged in a row. Further, in the flowchart shown in FIG. 12, the processes at steps S103 through S105 are repeatedly performed every time the operator changes the definition that he/she wishes to reference.

As explained above, according to the first embodiment, "MyoVector" is estimated on the basis of the hypothesis that the "moving directions of the individual tracking points obtained from the 3DT process substantially coincide with the directions of the myocardial fibers" and the objective fact that "the movement components in the radial (wall-thickness) direction are not movement components of the fiber directions", and further, the second movement information based on "MyoVector" is displayed.

With this arrangement, in the first embodiment, it is possible to present, to the user, the information related to the myocardial fiber directions and the information about the local movement components on the myocardial plane across which the myocardial fibers extend, by using the ultrasound image data having a higher time resolution than MRI images, by employing the ultrasound diagnosis apparatus, which is less expensive than an MRI apparatus. Consequently, according to the first embodiment, it is possible to conveniently present, in a non-invasive manner, the information related to the myocardial fiber directions and the information about the local movement components on the myocardial plane across which the myocardial fibers extend.

Further, in the first embodiment, because the second movement information is displayed in the 3D rendering display or the polar map display, the user is able to intuitively evaluate the appearance of the myocardial fiber directions. In addition, in the first embodiment, it is possible to obtain the information about the strain component in the myocardial fiber direction which is considered to better reflect physiological cardiac functions than the conventional three-axis strain component does. Furthermore, in the first embodiment, by calculating "MyoVector" and using the fourth output mode, it is possible to obtain, for example, the information about the shear strain rate or the shear strain between the endocardium and the epicardium, in addition to the conventional three-axis strain component.

Second Embodiment

Figures 13, 14:
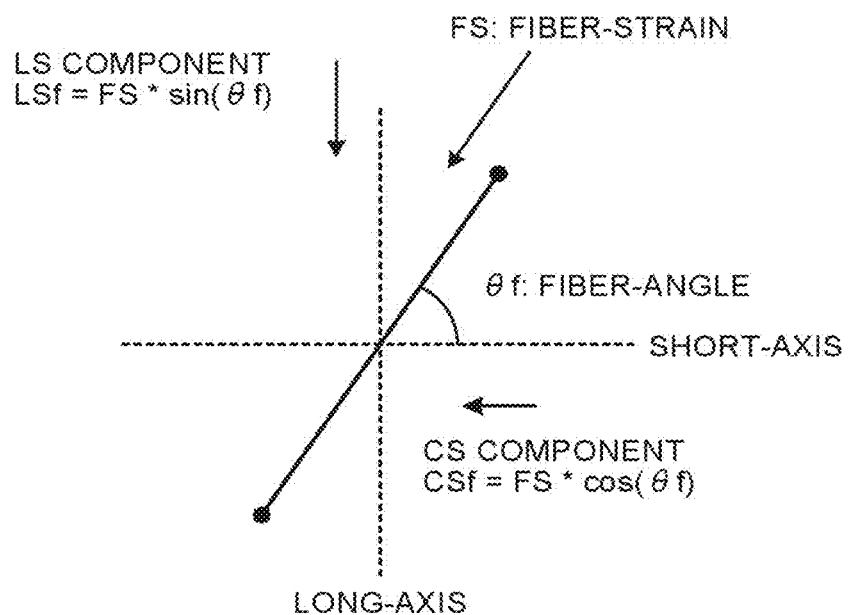
FIG. 13 is a drawing for explaining a second embodiment.
FIG. 14 is a drawing for explaining a third embodiment.

In the first embodiment, the examples were explained in which the motion vector obtained as the orthogonal projection component of the motion vector on the region of interest that is obtained from the tracking result is estimated as the myocardial fiber direction without applying any change thereto and in which the myocardial fiber direction is indirectly estimated on the basis of the motion vector obtained as the orthogonal projection component of the motion vector on the region of interest that is obtained from the tracking result. In a second embodiment, an example will be explained in which a myocardial fiber direction is estimated by implementing a method different from those in the first embodiment, with reference to mathematical formulae and FIG. 13 and so on. FIG. 13 is a drawing for explaining the second embodiment.

Estimation methods implemented in the second embodiment are roughly divided into two estimation methods. In the following sections, a first estimation method and a second estimation method will be explained, in the stated order.

The first estimation method is a method by which the determining unit 173 both estimates the direction information of a myocardial fiber and defines the second movement information, in a comprehensive manner. More specifically, according to the first estimation method, the determining unit 173 obtains a strain in the myocardial fiber direction by using a strain in the longitudinal direction and a strain in the circumferential direction that are obtained from the first movement information as local strains in the region of interest and further determines the obtained strain to be second movement information. In this situation, the LS and the CS values may be calculated by the calculating unit 171 or may be calculated by the determining unit 173.

As an example of the first estimation method, an example will be explained in which, while using the endocardial plane of the myocardium as a region of interest, LS in a local region in the longitudinal (long-axis) direction and CS in a local region in the short-axis direction are calculated by performing the 3DT process, so as to calculate the strain component in the myocardial fiber direction. In the following sections, the subscript "t" indicating the time (the temporal phase) will be omitted from the explanation.

When the cause-and-effect relationship is taken into consideration, a "fiber strain (FS)" occurs first, and "FS" is then separated by "$\theta f$", which is the fiber angle (the myocardial fiber angle) in the target position, into "LSf", which is a strain component in the longitudinal (long-axis) direction (an LS component) and "CSf", which is a strain component in the short-axis direction (a CS component). This relationship is illustrated in FIG. 13. The definition of the myocardial fiber angle explained below is the same as the definition explained in the first embodiment. The range of "$\theta f$" is set to "$-\pi/2$ to $\pi/2$".

In the present example, as illustrated in FIG. 13, it is observed that when "FS" corresponds to a contraction (a negative value), both "LSf" and "CSf" are each a negative value and that, in contrast, when "FS" corresponds to an expansion (a positive value), both "LSf" and "CSf" are each a positive value. Further, because the range of "$\theta f$" is set to "$-\pi/2$ to $\pi/2$", "$\cos(\theta f)$" is always a positive value, whereas the sign of "$\sin(\theta f)$" changes in accordance with that of "$\theta f$".

However, as illustrated in FIG. 13, because the signs of "LSf" and "CSf" are the same as each other, "sin(θf)" should always have a positive value. Accordingly, in the first estimation method, the negative side is not defined as the polarity of "θf". For this reason, according to the first estimation method, the mathematical formulae shown below are used while the range of "θf" is set to "0 to π/2".

While the range is set as described above, "LSf" and "CSf" can be expressed as shown in Expression (16) below and FIG. 13, by using "FS" and "θf".

$$\left.\begin{array}{l} LSf = FS*\sin(\theta f) \\ CSf = FS*\cos(\theta f) \end{array}\right\} \quad (16)$$

Thus, "LSf/CSf" can be expressed as shown in Expression (17) below by using "θf", whereas "θf" can be expressed as shown in Expression (18) below by using "LSf/CSf".

$$\left.\begin{array}{l} LSf/CSf = \tan(\theta f) \\ (\text{Where } CSf \neq 0) \end{array}\right\} \quad (17)$$

$$\left.\begin{array}{l} \theta f = \tan^{-1}(LSf/CSf) \\ (\text{Where } CSf \neq 0) \end{array}\right\} \quad (18)$$

It should be noted that Expressions (17) and (18) are valid under the condition "CSf≠0". If "CSf=0" is satisfied, "θf=π/2" is satisfied, because "θf≥0".

Accordingly, it is observed that when "LSf" and "CSf" are obtained, it is possible to obtain "FS" by assigning "θf" to Expression (16), "θf" being obtained on the basis of Expression (18) and the statement "if "CSf=0" is satisfied, θf=π/2 is satisfied". In this situation, if "CSf=0" is satisfied, "FS=LSf/sin(π/2)=LSf" is satisfied.

Thus, according to the first estimation method, in order to calculate backwards "FS" from the "CS" and the "LS" values obtained by performing the 3DT process, it is considered that "LSf=LS" and "CSf=CS" are satisfied under the condition "LS*CS≥0".

After that, the determining unit 173 calculates "FS" by assigning "LSf=LS" and "CSf=CS" to Expression (16). Alternatively, in the first estimation method, the obtaining unit 172 may estimate "θf=π/2" as the direction information of the myocardial fiber if "CS=0" is satisfied and may estimate "θf" obtained by assigning "LSf=LS" and "CSf=CS" to Expression (18) as the direction information of the myocardial fiber if "CS≠0" is satisfied, so as to output the estimated direction information to the determining unit 173.

In the present example, as mentioned in the additional explanation for the third output mode in the first embodiment, "CS" and "LS" observed during the 3DT process are not necessarily equal to "CSf" and "LSf". However, as for the meaning of the strain component in the fiber direction that takes the myocardial sheet sliding component into account, the strain component obtained on the basis of "LSf=LS" and "CSf=CS" also has the same meaning as the strain component explained as the third output mode in the first embodiment.

In the explanation above, "LS*CS≥0" is a condition for arranging the signs of "LSf" and "CSf" to be the same as each other. Thus, in the first estimation method, if the polarity of "LS" is different from the polarity of "CS" (i.e., if "LS*CS<0" is satisfied), "FS" is calculated backwards on the basis of "either a first concept or a second concept" explained below.

The strain component due to an expansion is observed in a medical case of a myocardial infarction or a heart failure with a degraded wall movement. The strain component due to an expansion in this situation is not an active contraction movement. In some situations, the strain component due to an expansion occurs as a passive expansion as a result of a "rivalry competition" with myocardial tissues in the surroundings. In other situations, the strain component due to an expansion occurs because of an expansion that occurs at a time when a contraction is supposed to occur due to an abnormality in the electric conduction system. The first concept is a concept for the process based on the former situations, whereas the second concept is a concept for the process based on the latter situations.

Because the contraction component of "FS" that is valid in the analysis has the negative polarity, the first concept puts importance on the negative side. According to the first concept, the determining unit 173 or the obtaining unit 172 performs the process indicated in Expression (19) shown below.

$$\left.\begin{array}{l} \text{If "}LS < 0 \text{ and } CS > 0\text{" is satisfied, } \theta f = \pi/2 \\ \text{If "}LS < 0 \text{ and } CS > 0\text{" is satisfied, } \theta f = 0 \end{array}\right\} \quad (19)$$

In other words, according to the first concept, as shown in Expression (19), if "LS<0 and CS>0" is satisfied, "θf=π/2" is assumed so that "FS=LS" having the negative polarity is obtained. In contrast, according to the first concept, as shown in Expression (19), if "LS>0 and CS<0" is satisfied, "θf=0" is assumed so that "FS=LS" having the negative polarity is obtained.

In contrast, the second concept is a process putting importance on the side having a larger absolute value. According to the second concept, the determining unit 173 or the obtaining unit 172 performs the process indicated in Expression (20) shown below.

$$\left.\begin{array}{l} \text{If "}|LS| > |CS|\text{" is satisfied, } \theta f = \pi/2 \\ \text{If "}|LS| > |CS|\text{" is satisfied, } \theta f = 0 \end{array}\right\} \quad (20)$$

In other words, according to the second concept, as shown in Expression (20), if "|LS|>|CS|" is satisfied, "θf=π/2" is assumed so that "FS=LS" can be satisfied. In contrast, according to the second concept, as shown in Expression (20), if "|LS|<|CS|" is satisfied, "θf=0" is assumed so that "FS=CS" can be satisfied.

According to the first estimation method, the determining unit 173 determines the "FS" value calculated backwards in the process described above to be the second movement information and outputs the second movement information to the controlling unit 18. The display mode of "FS" may be the same as the display mode explained for the third output mode in the first embodiment. Alternatively, according to the first estimation method, the determining unit 173 may determine "θf" to be the second movement information and output the second movement information to the controlling unit 18. The display mode of "θf" may be the same as the display mode explained for the second output mode in the first embodiment.

As explained above, the first estimation method is a method by which the second movement information "FS" defined with the use of the mathematical formulae on the basis of the myocardial fiber direction is calculated from "LS" and "CS" that have conventionally been used as indices of wall movements, without performing the process of estimating the myocardial fiber direction itself.

Next, the second estimation method will be explained. According to the second estimation method, the obtaining unit 172 obtains local strain information of the region of interest from the first movement information. More specifically, the obtaining unit 172 uses "LS" and "CS". After that, the obtaining unit 172 estimates direction information indicating the direction of a myocardial fiber, by using "LS" and "CS" that are obtained and a motion vector near the region of interest.

In other words, according to the second estimation method, the myocardial fiber direction is estimated by using information about the motion vector, together with "LS" and "CS".

In other words, the fundamental configuration of the second estimation method is the same as the first estimation method, but the second estimation method is configured to apply a polarity to the myocardial fiber angle "θf" in order to determine a myocardial fiber direction. For this reason, according to the second estimation method, the polarity of "θf" is estimated by using not only "LS" and "CS" at "P(t)", but also the motion vector at "P(t)".

In the present example, the second estimation method is based on hypothesis (0) explained in the first embodiment. Accordingly, the motion vector used for defining the polarity is the motion vector "V^(P(t))" obtained by performing the process explained in the first embodiment. In other words, according to the second estimation method, the obtaining unit 172 obtains "LS" and "CS" at "P(t)" and calculates the motion vector "V^(P(t))" at "P(t)" by performing the process explained in the first embodiment.

Further, in the same manner as in the process performed by the determining unit 173 in the second output mode in the first embodiment, the obtaining unit 172 calculates the angle "θ" formed by the vector "F(t)" in the fiber direction at the target position obtained from the motion vector "V^(P(t))" and, for example, the unit direction vector "c(t0)" in the circumferential direction on the short axis in the same target position in the reference temporal phase.

After that, the obtaining unit 172 extracts only polarity information "sign(θ)" from "θ", appends the extracted polarity information "sign(θ)" to the value of "θf" obtained from the same process as the process performed by the determining unit 173 in the first estimation method, and estimates a myocardial fiber angle "θ'" that is direction information of a myocardial fiber. More specifically, the obtaining unit 172 calculates the myocardial fiber angle "θ'f" by using Expression (21) shown below.

$$\theta'f = \text{sign}(\theta) * \theta f \quad (21)$$

After that, according to the second estimation method, the determining unit 173 determines the myocardial fiber angle "θ'f" to be second movement information and outputs the second movement information to the controlling unit 18. In addition, according to the second estimation method, the determining unit 173 calculates "FS" corresponding to a scalar of the vector by performing the process explained in the first estimation method, determines a vector in the fiber direction obtained by appending "sign(θ)" to "FS" to be the second movement information, and outputs the second movement information to the controlling unit 18. The vector in the fiber direction has the same meaning as the vector "F(t)" in the fiber direction explained in the first embodiment.

As explained above, according to the second estimation method, "θ'f" and the vector in the fiber direction obtained by appending "sign(θ)" to "FS" are output as the second movement information. Further, in the second estimation method, it is also acceptable to calculate and output a strain component in the myocardial fiber direction explained for the second output mode in the first embodiment by using the information about the vector in the myocardial fiber direction.

Alternatively, in the second estimation method, it is also acceptable to output "FS" that is calculated in the same manner as in the first estimation method, as a strain component in the myocardial fiber direction. The display mode for these final outputs may be implemented by using any of the various types of display methods explained in the first embodiment.

According to the second estimation method, the myocardial fiber direction is not estimated by using a motion vector as the main element. According to the second estimation method, the vector information of the myocardial fiber direction is estimated by calculating "FS" as the scalar quantity that serves as the main element of the vector in the myocardial fiber direction, on the basis of "LS and CS" that have conventionally been used, and by further complementing only the polarity thereof by using the information of the motion vector. The processes performed by the ultrasound diagnosis apparatus according to the second embodiment is similar to the processes shown in the flowchart in FIG. 12 except that the processes at steps S103 and S104 are replaced with the processes described above. Thus, the explanation thereof will be omitted.

As explained above, according to the second embodiment, like in the first embodiment, it is possible to conveniently present, in a non-invasive manner, the information related to the myocardial fiber directions and the information about the local movement components on the myocardial plane across which the myocardial fibers extend.

Third Embodiment

In the first and the second embodiments, the examples are explained in which the second movement information is output by estimating the direction information of the myocardial tissue and the myocardial tissue directions by using the first movement information obtained by performing the 3DT process. In a third embodiment, an example will be explained in which second movement information is output by providing direction information of the myocardial tissue and a myocardial tissue direction as user settings, with reference to FIG. 14 and so on. FIG. 14 is a drawing for explaining the third embodiment.

The obtaining unit 172 according to the third embodiment obtains direction information indicating the direction of a myocardial fiber, as information set by the operator. Further, by using the direction information set by the operator, the determining unit 173 extracts a movement component in the myocardial fiber direction from the first movement information and determines the second movement information by using the extracted movement component.

In the third embodiment, in a preferable example, the operator sets a fiber angle "θ" as the myocardial fiber direction. For example, as illustrated in FIG. 14, on the basis of anatomical observations that are known, the operator sets "θ=+60 degrees" when the region of interest is the endocardial plane, sets "θ=−60 degrees" when the region of interest is the epicardial plane, and sets "θ=0 degrees" when the region of interest is the intermediate layer plane.

In this situation, when the fiber angle "θ" set by the user is given at each of the tracking points "P(t)", the fiber angle can be expressed as "θ(P(t))". In the example illustrated in FIG. 14, because mutually the same value is uniformly given as the fiber angle in the entirety of the region of interest serving as the target, "θ(P(t))" exhibits the same value at all the points "P(t)". The example described above is the simplest application example.

It should be noted, however, that in the third embodiment, it is desirable for the operator to provide the obtaining unit 172 with "θ(P(t))" expressing a fiber angle value that varies in accordance with the positions of the tracking points and the temporal phases, while taking into account the local distribution of fiber angles within the region of interest and temporal changes. To realize such a "θ(P(t))" value, the operator sets "θ(P(t))" by referring to a value estimated in advance by implementing a publicly-known method that uses MRI or sets a value presumed from known anatomical observations (e.g., information from textbooks) as an estimated value.

The determining unit 173 is able to extract, as the second movement information, information (the direction and the magnitude) of "MyoVector" that is a component of the motion vector with respect to the myocardial fiber direction set by the user and is further able to extract, as the second movement information, a strain component with respect to the myocardial fiber direction set by the user. It is possible to display the information that is output as a result of these processes, by implementing any of the various methods explained in the first and the second embodiments.

In the first and the second embodiments, the direction information of the myocardial fibers is automatically estimated by using the various methods described above. There is a possibility, however, that in some situations, the automatic estimation of the myocardial fiber directions via the first movement information may not function well, in a medical case where the image quality of the time-series data to be analyzed is low or due to an impact of local artifacts occurring in the time-series data to be analyzed.

In those situations where the reliability of the automatic estimation is low, it is desirable to obtain the second movement information from the user setting as described above. By using the user setting described above, it is possible to even more conveniently present the information related to the myocardial fiber directions in a non-invasive manner.

It is also acceptable to apply the modification example described below to the third embodiment. In the present modification example, basically, the direction information of the myocardial fibers is automatically estimated like in the first and the second embodiments, and the setting by the user about the direction information of the myocardial fibers is received for necessary data and necessary locations as described above, so that a calculation is performed while switching between the inputs of direction information to be used in the internal process.

In the present modification example, however, when switching between the inputs, there may be some boundary regions, spatially and temporally, where the pieces of input information used for defining the second movement information are locally different from each other. For this reason, in the present modification example, it is desirable to, in such boundary regions, smoothly connect the pieces of direction information of the myocardial fibers between the two boundary regions by performing a spatial smoothing process and a temporal smoothing process, before performing the process at the subsequent stage.

The process performed in the present modification example can be summarized as below, while referring to the direction information of the myocardial fibers that is automatically estimated in the first and the second embodiments as first direction information and referring to the direction information of the myocardial fibers set by the user as second direction information:

The obtaining unit 172 according to the present modification example obtains third direction information indicating directions of myocardial fibers by using the first direction information and the second direction information. More specifically, the obtaining unit 172 according to the present modification example obtains the third direction information that is the direction information of the myocardial fibers, by smoothly switching from the first direction information to the second direction information, in a boundary between predetermined spatiotemporal regions in the region of interest. In this situation, the "boundary between predetermined spatiotemporal regions" is a boundary between spatiotemporal regions in which the precision level in the estimation of the first direction information that is automatically estimated is degraded. After that, the determining unit 173 according to the present modification example determines the second movement information by using the third direction information.

The "boundary between the spatiotemporal regions" may be set by the operator by, for example, specifying a space or a temporal phase of which the operator has determined that the precision level in the estimation of the first direction information is degraded because of a low reliability of the first movement information, by referring to the group of three-dimensional ultrasound image data or referring to MPR image data on which a distribution of indices such as a CS value is superimposed in color. Alternatively, the "boundary between the spatiotemporal regions" may be set as a result of an automatic assessment by the controlling unit 18 that uses, for example, the brightness levels of the group of three-dimensional ultrasound image data or a signal-to-noise (S/N) ratio of the reception signals. In one of the most desirable examples, an index of reliability for estimating the motion vectors by implementing the speckle tracking method may be used. As for the index of reliability, various types of indices are known, such as image brightness levels, a brightness variance, similarities in pattern matching, and the like. In that situation, the obtaining unit 172 provides the third direction information obtained by averaging the first direction information and the second direction information while varying the weights thereof in accordance with the reliability of the movement. In other words, the obtaining unit 172 obtains the third direction information indicating the directions of the myocardial fibers by performing a weighted addition on the first direction information and the second direction information in accordance with the reliability of the first movement information.

According to the present modification example, it is possible to present, conveniently and with certainty, the information related to the myocardial fiber directions and the information about the local movement components on the myocardial plane across which myocardial fibers extend, in a non-invasive manner.

Fourth Embodiment

Figure 15:
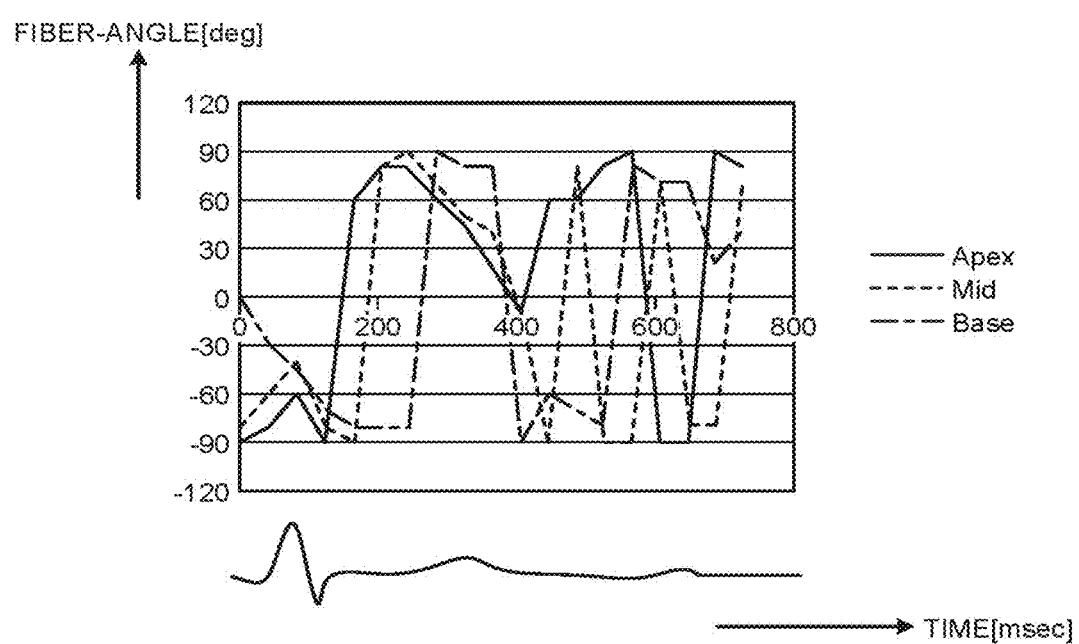
FIG. 15 is a drawing for explaining a fourth embodiment.

In a fourth embodiment, a modification example related to the output display of the second movement information will be explained, with reference to FIG. 15 and so on. FIG. 15 is a drawing for explaining the fourth embodiment.

As explained above, when a plurality of regions of interest are set, the obtaining unit 172 obtains the direction information indicating the direction of a myocardial fiber for each of the plurality of regions of interest. Further, in the fourth embodiment, the determining unit 173 determines information obtained by calculating a difference between the regions of interest by using the pieces of second movement information obtained for the plurality of regions of interest, to be new second movement information.

For example, the determining unit 173 obtains a difference between pieces of movement information corresponding to fiber directions on two arbitrary planes selected from the endocardial plane, the epicardial plane, and the intermediate layer plane. In one example, the determining unit 173 determines and outputs a difference fiber angle obtained by subtracting a fiber angle of the endocardium from a fiber angle of the epicardium to be new second movement information.

Specific examples of the display mode for the difference information include an example in which time-change curves of the difference information in units of segments are displayed and an example in which the difference information is displayed in a 3D rendering display by assigning colors thereto. Further, in other examples of the display mode for the difference information, any of the various types of display methods explained in the first to the third embodiments is applicable to the new second movement information obtained by calculating the difference.

Alternatively, in the fourth embodiment, the controlling unit 18 may cause the monitor 2 to display a time-change curve of the myocardial fiber angle in at least one region defined within the region of interest. For example, in the fourth embodiment, time-change curves of the myocardial fiber angle "θ(t)" in units of segments may be displayed in a chart, as illustrated in FIG. 15, like the strains or the like used as a conventional wall-movement index.

In the chart illustrated in FIG. 15, the horizontal axis expresses time, whereas the vertical axis expresses the myocardial fiber angle. Temporal changes in the fiber angle in the segments of three locations such as the apex ("Apex"), the intermediate part ("Mid"), and the base ("Base") of the heart are displayed, together with an electrocardiogram. As for the segments used for the time-change curves of the myocardial fiber angle, any of the anterior wall, the septum, the lateral wall, the posterior wall, and the inferior wall, may be used. In this situation, as observed from the chart in FIG. 15, the plotted line expressing the range of "θ(t)" exhibits aliasing at "±90 degrees". Further, in a chart showing a time-change curve of "MyoVector" which is a motion vector or a streamline vector, the plotted line exhibits aliasing at "±180 degrees", for example.

To cope with these situations, when displaying the chart showing the time-change curves, for example, the controlling unit 18 eliminates aliasing of the plotted lines by performing an "unwrapping process", the unwrapping process is commonly used as a joining process when phase aliasing occurs. Alternatively, the controlling unit 18 may display a chart while preventing the plotted line from aliasing near the angle parallel to the short axis or the long axis, by adding a predetermined offset component to the myocardial fiber angle, in advance.

As explained above, in the fourth embodiment, it is possible to provide the user with the information related to the directions of the myocardial fibers in the various modes. For example, by referring to the difference information, the user is able to easily recognize the regions in which the movement directions of the myocardial fibers are different, between the endocardium and the epicardium. Further, for example, by referring to the chart showing the time-change curves of the myocardial fiber angles corresponding to the segments, the user is able to easily recognize the parts where the movements of the myocardial fibers are out of synchronization.

In the first to the fourth embodiments described above, the examples are explained in which the ultrasound diagnosis apparatus performs the image processing processes that use the group of three-dimensional ultrasound image data of the heart. However, the image processing processes described in any of the first to the fourth embodiments above may be performed by an image processing apparatus that is provided independently of the ultrasound diagnosis apparatus. More specifically, an image processing apparatus having the functions of the image processing unit 17, the controlling unit 18, and the like may perform the image processing processes explained above by receiving the group of three-dimensional ultrasound image data of the heart from the ultrasound diagnosis apparatus, a Picture Archiving and Communication System (PACS) database, a database in an electronic medical record system, or the like.

Further, the image processing processes described in any of the first to the fourth embodiments above may be performed on not only the group of three-dimensional ultrasound image data of the heart, but also a group of three-dimensional medical image data acquired by an X-ray Computed Tomography (CT) Apparatus, an MRI apparatus, or the like. In that situation, the image processing processes performed on the group of three-dimensional medical image data of the heart may be performed by the medical image diagnosis apparatus that acquired the data or may be performed by the abovementioned image processing apparatus.

In the first to the fourth embodiments described above, the examples are explained in which the image processing processes are performed for outputting and displaying the second movement information while the left ventricle is used as the target. However, the image processing processes described in any of the first to the fourth embodiments above are also applicable to any of the other chambers of the heart (i.e., the left atrium, the right atrium, and the right ventricle) besides the left ventricle, although researches have not yet progressed very much. Thus, also for the other chambers, it is possible to present analysis results that are similar to those of the left ventricle.

Further, the constituent elements of the apparatuses that are illustrated in the drawings in the first to the fourth embodiments are based on functional concepts. Thus, it is not necessary to physically configure the elements as indicated in the drawings. In other words, the specific mode of distribution and integration of the apparatuses is not limited to the ones illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a Central Processing Unit (CPU) and a computer program that is analyzed and executed by the CPU or may be realized as hardware using wired logic.

Furthermore, the image processing methods explained in the first to the fourth embodiments may be realized by causing a computer such as a personal computer or a workstation to execute an image processing computer program (hereinafter, an "image processing program") that is prepared in advance. The image processing program may be distributed via a network such as the Internet. Further, it is also possible to record the image processing program onto a computer-readable non-transitory recording medium such as a hard disk, a flexible disk (FD), a Compact Disk Read-Only Memory (CD-ROM), a Magneto-optical (MO) disk, a Digital Versatile Disk (DVD), or the like, so that a computer is able to read the program from the recording medium and to execute the read program.

As explained above, according to at least one aspect of the first to the fourth embodiments, it is possible to conveniently present, in a non-invasive manner, the information related to the myocardial fiber directions and the information about the local movement components on the myocardial plane across which the myocardial fibers extend.

While certain embodiments have been described, these embodiments have been presented by way of example only, and are not intended to limit the scope of the inventions. Indeed, the novel embodiments described herein may be embodied in a variety of other forms, furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising processing circuitry configured to:
   set a region of interest in a myocardium of a subject for each of a plurality of pieces of three-dimensional ultrasound image data in a time series corresponding to a three-dimensional region including the myocardium;
   calculate a three-dimensional motion vector at each individual tracking point by performing a process including pattern matching with the plurality of pieces of three-dimensional ultrasound image data in order to track movement of a plurality of tracking points structuring the region of interest;
   extract a vector component in a direction of a short-axis plane of the region of interest from the three-dimensional motion vector;
   calculate, as a translation movement component of the myocardium, an average motion vector of the extracted vector component in the direction of the short-axis plane;
   determine movement information indicating a movement of the myocardium in a contraction direction, by subtracting the translation movement component from the three-dimensional motion vector at each individual tracking point; and
   cause a display to display the movement information.

2. The ultrasound diagnosis apparatus according to claim 1, wherein the region of interest includes at least one of an endocardium of the myocardium, an epicardium of the myocardium, and an intermediate layer of the myocardium.

3. The ultrasound diagnosis apparatus according to claim 1, wherein the processing circuitry is further configured to
   perform the process including the pattern matching to calculate local strain information on the region of interest; and
   determine the movement information by using the calculated strain information and the three-dimensional motion vector near the region of interest.

4. The ultrasound diagnosis apparatus according to claim 1, wherein, with respect to a temporal phase in which a magnitude of the three-dimensional motion vector is smaller than a predetermined threshold value, the processing circuitry estimates a direction of the three-dimensional motion vector in the temporal phase by performing a temporal interpolation process.

5. The ultrasound diagnosis apparatus according to claim 1, wherein the processing circuitry is further configured to:
   determine at least one streamline as the movement information through a spatial interpolation process in a vector field formed by the three-dimensional motion vector on the boundary plane, the streamline being obtained from at least one starting point set on the boundary plane; and
   display a line corresponding to said at least one streamline in a superimposed manner on either three-dimensional rendering image data of the region of interest or a polar map of a heart.

6. The ultrasound diagnosis apparatus according to claim 5, wherein the processing circuitry causes either a line segment or an arrow indicating the direction of the individual motion vector in a vector field formed on the boundary plane and having a regulated length to be displayed in a superimposed manner on either three-dimensional rendering image data of the region of interest or a polar map of a heart.

7. The ultrasound diagnosis apparatus according to claim 1, wherein, by using vector information on a projection component of the three-dimensional motion vector on a first boundary plane, the three-dimensional motion vector being obtained on the first boundary plane in the region of interest, and vector information on a projection component of the three-dimensional motion vector on a secondary boundary plane, the three-dimensional motion vector being obtained on the second boundary plane in the region of interest, the processing circuitry estimates either a shear strain rate or a shear strain between the first boundary plane and the second boundary plane.

8. The ultrasound diagnosis apparatus according to claim 1, wherein the processing circuitry causes an index related to a local wall movement in the region of interest to be displayed simultaneously, together with the movement information.

9. The ultrasound diagnosis apparatus according to claim 1, wherein the processing circuitry is further configured to:
   when a plurality of regions of interest are each set as the region of interest, calculate the three-dimensional motion vector for each of the plurality of regions of interest;
   determine the movement information for each of the plurality of regions of interest; and
   cause the movement information corresponding to the plurality of regions of interest to be displayed simultaneously.

10. The ultrasound diagnosis apparatus according to claim 1, wherein the processing circuitry is further configured to:
    when a plurality of regions of interest are each set as the region of interest, calculate the three-dimensional motion vector for each of the plurality of regions of interest; and
    determine information obtained by calculating a difference between the regions of interest by using the movement information obtained for the plurality of regions of interest, to be new movement information.

11. An image processing apparatus comprising processing circuitry configured to:
    set a region of interest in a myocardium of a subject for each of a plurality of pieces of three-dimensional ultrasound image data in a time series corresponding to a three-dimensional region including the myocardium;

calculate a three-dimensional motion vector at each individual tracking point by performing a process including pattern matching with the plurality of pieces of three-dimensional ultrasound image data in order to track movement of a plurality of tracking points structuring the region of interest;

extract a vector component in a direction of a short-axis plane of the region of interest from the three-dimensional motion vector;

calculate, as a translation movement component of the myocardium, an average motion vector of the extracted vector component in the direction of the short-axis plane;

determine movement information indicating a movement of the myocardium in a contraction direction, by subtracting the translation movement component from the three-dimensional motion vector at each individual tracking point; and cause a display to display the movement information.

* * * * *